(12) United States Patent
Roe et al.

(10) Patent No.: US 7,982,088 B2
(45) Date of Patent: *Jul. 19, 2011

(54) DISPOSABLE ARTICLE HAVING A BIOSENSOR

(75) Inventors: Donald Carroll Roe, West Chester, OH (US); Andreas Muscat, Schwalbach (DE)

(73) Assignee: The Procter & Gamble Company, Cincinnati, OH (US)

( * ) Notice: Subject to any disclaimer, the term of this patent is extended or adjusted under 35 U.S.C. 154(b) by 116 days.

This patent is subject to a terminal disclaimer.

(21) Appl. No.: 10/753,669

(22) Filed: Jan. 8, 2004

(65) Prior Publication Data

US 2004/0172000 A1    Sep. 2, 2004

Related U.S. Application Data

(63) Continuation of application No. 09/299,399, filed on Apr. 26, 1999, now Pat. No. 6,713,660, which is a continuation-in-part of application No. 09/107,563, filed on Jun. 29, 1998, now Pat. No. 6,093,869.

(51) Int. Cl.
*A61F 13/15* (2006.01)

(52) U.S. Cl. ......... 604/361; 604/362; 604/367; 604/368
(58) Field of Classification Search ............... 604/361, 604/362, 367, 368; 600/306, 362, 359; 607/40, 607/41

See application file for complete search history.

(56) References Cited

U.S. PATENT DOCUMENTS

| 5,140,393 | A | * | 8/1992 | Hijikihigawa et al. | ....... 257/252 |
| 5,458,140 | A | * | 10/1995 | Eppstein et al. | ............... 600/573 |
| 5,468,236 | A | | 11/1995 | Everhart et al. | ............... 604/361 |
| 6,203,496 | B1 | | 3/2001 | Gael et al. | |

FOREIGN PATENT DOCUMENTS

| EP | 0 560 099 | 9/1993 |
| JP | 10-313894 | 12/1998 |
| WO | WO 94/24557 | 10/1994 |
| WO | WO 97/34014 | 9/1997 |
| WO | WO 98/27417 | 6/1998 |
| WO | WO 99/31486 | 6/1999 |

* cited by examiner

*Primary Examiner* — Jacqueline F Stephens
(74) *Attorney, Agent, or Firm* — William E. Gallagher; Thibault Fayette; Jay A. Krebs

(57) ABSTRACT

A disposable article to be fitted to a wearer comprising a biosensor including at least one bio-recognition element. The biosensor is adapted to detect a target biological analyte in bodily waste or on the wearer's skin.

45 Claims, 8 Drawing Sheets

DISPOSABLE ARTICLE HAVING A BIOSENSOR

CROSS REFERENCE TO RELATED APPLICATIONS

This application is a continuation of U.S. application Ser. No. 09/299,399, filed Apr. 26, 1999, now U.S. Pat. No. 6,713,660, which is a continuation-in-part of U.S. application Ser. No. 09/107,563, filed on Jun. 29, 1998 now U.S. Pat. No. 6,093,869.

FIELD OF THE INVENTION

The present invention relates to disposable articles and, more particularly, to disposable articles having biosensors having a bio-recognition element that detects microorganisms and/or other biomolecules in bodily waste.

BACKGROUND OF THE INVENTION

Today, disposable articles, such as diapers, adult incontinence briefs, sanitary napkins and tampons, are widely used in infant and toddler care and in the care of incontinent adults as a means of containing, isolating and disposing of bodily wastes. These articles have generally replaced reusable, washable cloth garments as the preferred means for these applications because of their convenience and reliability. The disposable articles respond to a defecation, urination or discharge event by absorbing or containing bodily wastes deposited on the article. Some disposable articles also signal a defecation, urination or discharge event after it has occurred (e.g., wetness indicators, temperature change detection). Other disposable absorbent articles known in the art comprise a chemically reactive means to detect various substances in the wearer's waste(s). However, none of these specifically detect target potentially pathogenic microorganisms such as bacteria, viruses, fungi, and parasites (e.g., protozoans) and/or related biomolecules, all of which require a high degree of selectivity (i.e., specificity) and sensitivity versus purely chemical agents. Additionally, the articles do not predict when a health-related event is about to occur and signal wearer or caregiver that prophylactic or remedial action is required prior to the onset of clinically observable symptoms.

SUMMARY OF THE INVENTION

The present invention is directed to a disposable article to be fitted to a wearer comprising a biosensor including at least one bio-recognition element. The biosensor is adapted to detect a target biological analyte in bodily waste or on the wearer's skin. More preferably, the absorbent article of the present invention may comprise a biosensor adapted to detect one or more specific microorganisms and/or related biomolecules and to signal the caretaker, the wearer, or an actuator of the occurrence.

DETAILED DESCRIPTION OF THE INVENTION

As used herein, the term "absorbent article" refers to devices which absorb and contain body exudates, and more specifically, refers to devices which are placed against or in proximity to the body of the wearer to absorb and contain the various exudates discharged from the body. The term "disposable" is used herein to describe absorbent articles which generally are not intended to be laundered or otherwise restored or reused as an absorbent article (i.e., they are intended to be discarded after a single use and, preferably, to be recycled, composted or otherwise disposed of in an environmentally compatible manner). (As used herein, the term "disposed" is used to mean that an element(s) of the diaper is formed (joined and positioned) in a particular place or position as a unitary structure with other elements of the diaper or as a separate element joined to another element of the diaper. As used herein, the term "joined" encompasses configurations whereby an element is directly secured to another element by affixing the element directly to the other element, and configurations whereby an element is indirectly secured to another element by affixing the element to intermediate member(s) which in turn are affixed to the other element.) A "unitary" absorbent article refers to absorbent articles which are formed of separate parts united together to form a coordinated entity so that they do not require separate manipulative parts like a separate holder and liner. A preferred embodiment of an absorbent article of the present invention is a unitary disposable absorbent article, such as the diaper 20 shown in FIG. 1. As used herein, the term "diaper" refers to an absorbent article generally worn by infants and incontinent persons about the lower torso. The present invention is also applicable to other absorbent or non-absorbent articles such as incontinence briefs, incontinence undergarments, absorbent inserts, diaper holders and liners, colostomy bags for a natural or artificial anus, feminine hygiene garments, tampons, wipes, disposable towels, tissues, water absorbing articles, oil absorbing articles, spill cleanup bags, desiccant bags, disposable mops, bandages, therapeutic wraps, supports, disposable heating pads and the like.

Figure 1:
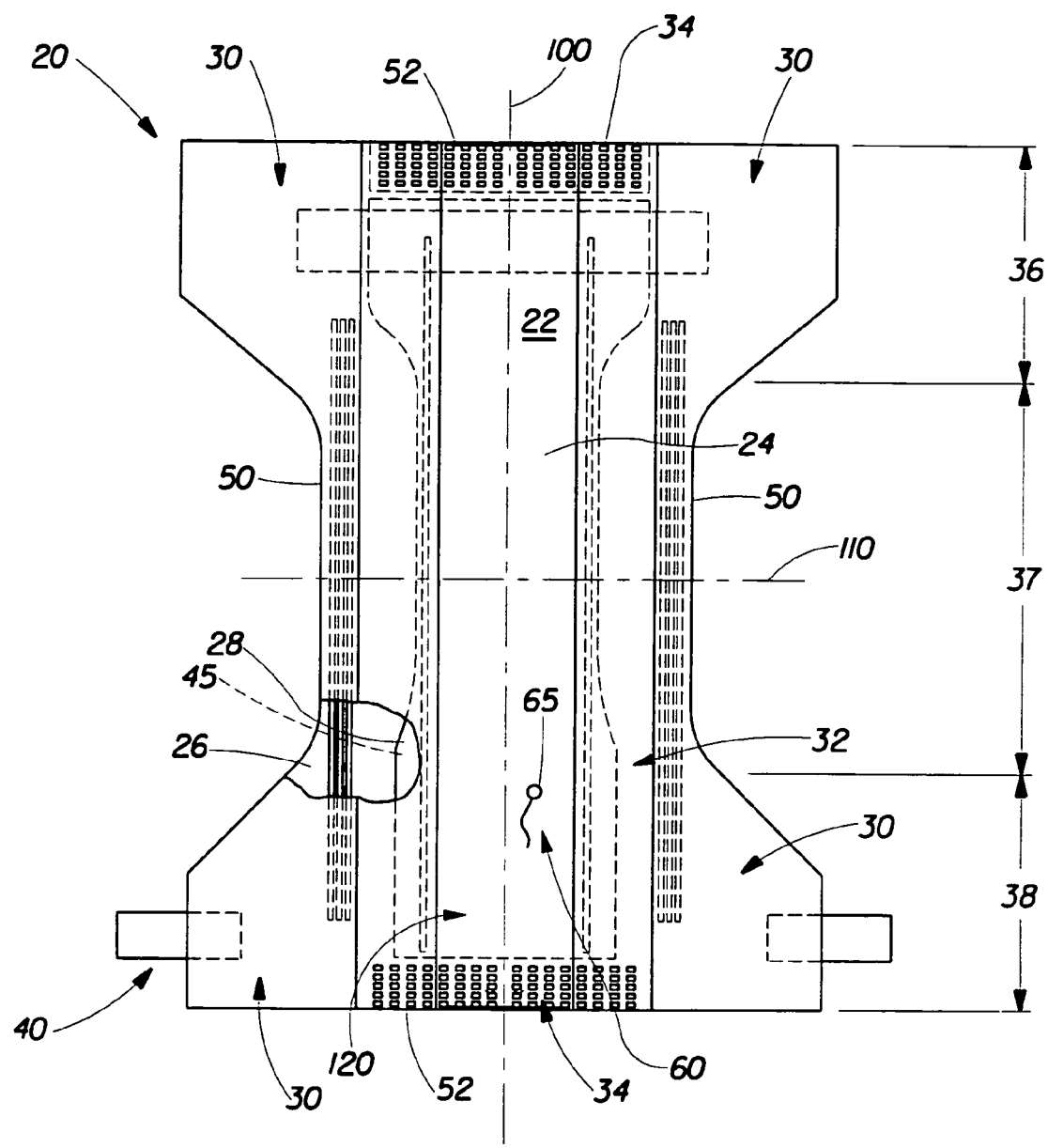
FIG. 1 is a plan view of the article made in accordance with the present invention in a flat-out state with portions of the structure being cut-away to more clearly show the construction of the article, wherein the article is a diaper.

FIG. 1 is a plan view of the diaper 20 of the present invention in a flat-out, state with portions of the structure being cut-away to more clearly show the construction of the diaper 20. The portion of the diaper 20 which faces the wearer is oriented towards the viewer. As shown in FIG. 1, the diaper 20 preferably comprises a liquid pervious topsheet 24; a liquid impervious backsheet 26; an absorbent core 28, which is preferably positioned between at least a portion of the topsheet 24 and the backsheet 26; side panels 30; elasticized leg cuffs 32; an elastic waist feature 34; and a fastening system generally designated 40. Diaper 20 is shown in FIG. 1 to have a first waist region 36, a second waist region 38 opposed to the first waist region 36 and a crotch region 37 located between the first waist region and the second waist region. The periphery of the diaper 20 is defined by the outer edges of the diaper 20 in which the longitudinal edges 50 run generally parallel to the longitudinal centerline 100 of the diaper 20 and the end edges 52 run between the longitudinal edges 50 generally parallel to the lateral centerline 110 of the diaper 20.

The chassis 22 of the diaper 20 comprises the main body of the diaper 20. The chassis 22 comprises at least a portion of the absorbent core 28 and preferably an outer covering layer including the topsheet 24 and the backsheet 26. If the absorbent article comprises a separate holder and a liner, the chassis 22 generally comprises the holder and the liner. (For example, the holder may comprise one or more layers of material to form the outer cover of the article and the liner may comprise an absorbent assembly including a topsheet, a backsheet, and an absorbent core. In such cases, the holder and/or the liner may include a fastening element which is used to hold the liner in place throughout the time of use.) For unitary absorbent articles, the chassis 22 comprises the main structure of the diaper with other features added to form the composite diaper structure. While the topsheet 24, the backsheet 26, and the absorbent core 26 may be assembled in a variety of well known configurations, preferred diaper configurations are described generally in U.S. Pat. No. 3,860,003 entitled "Contractible Side Portions for Disposable Diaper" which issued to Kenneth B. Buell on Jan. 14, 1975; U.S. Pat. No. 5,151,092 issued to Buell on Sep. 9, 1992; and U.S. Pat. No. 5,221,274 issued to Buell on Jun. 22, 1993; and U.S. Pat. No. 5,554,145 entitled "Absorbent Article With Multiple Zone Structural Elastic-Like Film Web Extensible Waist Feature" which issued to Roe et al. on Sep. 10, 1996; U.S. Pat. No. 5,569,234 entitled "Disposable Pull-On Pant" which issued to Buell et al. on Oct. 29, 1996; U.S. Pat. No. 5,580,411 entitled "Zero Scrap Method For Manufacturing Side Panels For Absorbent Articles" which issued to Nease et al. on Dec. 3, 1996; and U.S. patent application Ser. No. 08/915,471 entitled "Absorbent Article With Multi-Directional Extensible Side Panels" filed Aug. 20, 1997 in the name of Robles et al.; each of which is incorporated herein by reference.

The backsheet 26 is generally that portion of the diaper 20 positioned adjacent the garment facing surface 45 of the absorbent core 28 which prevents the exudates absorbed and contained therein from soiling articles which may contact the diaper 20, such as bedsheets and undergarments. The backsheet 26 may be joined to the topsheet 24, the absorbent core 28 or any other element of the diaper 20 by any attachment means known in the art. Suitable backsheet films include those manufactured by Tredegar Industries Inc. of Terre Haute, Ind. and sold under the trade names X15306, X10962 and X10964. Other suitable backsheet materials may include breathable materials such as woven webs, nonwoven webs, composite materials such as film-coated nonwoven webs, and microporous films such as manufactured by Mitsui Toatsu Co., of Japan under the designation ESPOIR NO; EXXON Chemical Co., of Bay City, Tex., under the designation EXXAIRE; or monolithic films such as manufactured by Clopay Corporation, Cincinnati, Ohio under the name HYTREL blend P18-3097. Such breathable composite materials are described in greater detail in PCT Application No. WO 95/16746, published on Jun. 22, 1995 in the name of E. I. DuPont; copending U.S. Pat. No. 5,865,823 issued to Curro on Feb. 2, 1999; U.S. Pat. No. 5,571,096 issued to Dobrin et al. on Nov. 5, 1996. Each of these references is hereby incorporated by reference herein.

The backsheet 26, or any portion thereof, may be elastically extensible in one or more directions. In one embodiment, the backsheet 26 may comprise a structural elastic-like film ("SELF") web. A structural elastic-like film web is an extensible material that exhibits an elastic-like behavior in the direction of elongation without the use of added elastic materials. SELF webs suitable for the present invention are described in U.S. Pat. No. 5,518,801 entitled Web Materials Exhibiting Elastic-Like Behavior, which issued to Chappell, et, al. on May 21, 1996, which is incorporated herein by reference. In alternate embodiments, the backsheet 26 may comprise elastomeric films, foams, strands, or combinations of these or other suitable materials with nonwovens or synthetic films.

The topsheet 24 is preferably compliant, soft feeling, and non-irritating to the wearer's skin. A suitable topsheet 24 may be manufactured from a wide range of materials, such as porous foams; reticulated foams; apertured plastic films; or woven or nonwoven webs of natural fibers (e.g., wood or cotton fibers), synthetic fibers (e.g., polyester or polypropylene fibers), or a combination of natural and synthetic fibers. If the topsheets include fibers, the fibers may be spunbond, carded, wet-laid, meltblown, hydroentangled, or otherwise processed as is known in the art. One suitable topsheet 24 comprising a web of staple length polypropylene fibers is manufactured by Veratec, Inc., a Division of International Paper Company, of Walpole, Massachusetts under the designation P-8.

Suitable formed film topsheets are described in U.S. Pat. No. 3,929,135, entitled "Absorptive Structures Having Tapered Capillaries", which issued to Thompson on Dec. 30, 1975; U.S. Pat. No. 4,324,246 entitled "Disposable Absorbent Article Having A Stain Resistant Topsheet", which issued to Mullane, et al. on Apr. 13, 1982; U.S. Pat. No. 4,342,314 entitled "Resilient Plastic Web Exhibiting Fiber-Like Properties", which issued to Radel, et al. on Aug. 3, 1982; U.S. Pat. No. 4,463,045 entitled "Macroscopically Expanded Three-Dimensional Plastic Web Exhibiting Non-Glossy Visible Surface and Cloth-Like Tactile Impression", which issued to Ahr, et al. on Jul. 31, 1984; and U.S. Pat. No. 5,006,394 "Multilayer Polymeric Film" issued to Baird on Apr. 9, 1991. Other suitable topsheets 30 are made in accordance with U.S. Pat. Nos. 4,609,518 and 4,629,643 which issued to Curro et al. on Sep. 2, 1986 and Dec. 16, 1986, respectively, and both of which are incorporated herein by reference. Such formed films are available from The Procter & Gamble Company of Cincinnati, Ohio as "DRI-WEAVE" and from Tredegar Corporation of Terre Haute, Ind. as "CLIFF-T."

Preferably, the topsheet 24 is made of a hydrophobic material or is treated to be hydrophobic in order to isolate the wearer's skin from liquids contained in the absorbent core 28. If the topsheet 24 is made of a hydrophobic material, preferably at least the upper surface of the topsheet 24 is treated to be hydrophilic so that liquids will transfer through the topsheet more rapidly. The topsheet 24 can be rendered hydrophilic by treating it with a surfactant or by incorporating a surfactant into the topsheet. Suitable methods for treating the topsheet 24 with a surfactant include spraying the topsheet 24 material with the surfactant and immersing the material into the surfactant. A more detailed discussion of such a treatment and hydrophilicity is contained in U.S. Pat. No. 4,988,344 entitled "Absorbent Articles with Multiple Layer Absorbent Layers" issued to Reising, et al. on Jan. 29, 1991 and U.S. Pat. No. 4,988,345 entitled "Absorbent Articles with Rapid Acquiring Absorbent Cores" issued to Reising on Jan. 29, 1991. A more detailed discussion of some suitable methods for incorporating surfactant in the topsheet can be found in U.S. Statutory Invention Registration No. H1670, published on Jul. 1, 1997 in the names of Aziz et al. Each of these references is hereby incorporated by reference herein.

Any portion of the topsheet 24 or other components of the article may be coated with a lotion as is known in the art. Examples of suitable lotions include those described in U.S. Pat. No. 5,607,760 entitled "Disposable Absorbent Article Having A Lotioned Topsheet Containing an Emollient and a Polyol Polyester Imobilizing Agent" which issued to Roe on Mar. 4, 1997; U.S. Pat. No. 5,609,587 entitled "Diaper Having A Lotion Topsheet Comprising A Liquid Polyol Polyester Emollient And An Immobilizing Agent" which issued to Roe on Mar. 11, 1997; U.S. Pat. No. 5,635,191 entitled "Diaper Having A Lotioned Topsheet Containing A Polysiloxane Emollient" which issued to Roe et al. on Jun. 3, 1997; and U.S. Pat. No. 5,643,588 entitled "Diaper Having A Lotioned Topsheet" which issued to Roe et al. on Jul. 1, 1997. The lotion may function alone or in combination with another agent as the hydrophobizing treatment described above. The topsheet may also include or be treated with antibacterial agents, some examples of which are disclosed in PCT Publication No. WO 95/24173 entitled "Absorbent Articles Containing Antibacterial Agents in the Topsheet For Odor Control" which was published on Sep. 14, 1995 in the name of Theresa Johnson. Further, the topsheet 24, the backsheet 26 or any portion of the topsheet or backsheet may be embossed and/or matte finished to provide a more cloth like appearance.

The absorbent core 28 may comprise any absorbent material which is generally compressible, conformable, non-irritating to the wearer's skin, and capable of absorbing and retaining liquids such as urine and other certain body exudates. The absorbent core 28 may be manufactured in a wide variety of sizes and shapes (e.g., rectangular, hourglass, "T"-shaped, asymmetric, etc.) and may comprise a wide variety of liquid-absorbent materials commonly used in disposable diapers and other absorbent articles such as comminuted wood pulp, which is generally referred to as airfelt. Examples of other suitable absorbent materials include creped cellulose wadding; meltblown polymers, including coform; chemically stiffened, modified or cross-linked cellulosic fibers; tissue, including tissue wraps and tissue laminates; absorbent foams; absorbent sponges; superabsorbent polymers; absorbent gelling materials; or any other known absorbent material or combinations of materials.

The configuration and construction of the absorbent core 28 may also be varied (e.g., the absorbent core(s) or other absorbent structure(s) may have varying caliper zones, a hydrophilic gradient, a superabsorbent gradient, or lower average density and lower average basis weight acquisition zones; or may comprise one or more layers or structures).

Exemplary absorbent structures for use as the absorbent assemblies are described in U.S. Pat. No. 4,610,678 entitled "High-Density Absorbent Structures" issued to Weisman et al. on Sep. 9, 1986; U.S. Pat. No. 4,673,402 entitled "Absorbent Articles With Dual-Layered Cores" issued to Weisman et al. on Jun. 16, 1987; U.S. Pat. No. 4,834,735, entitled "High Density Absorbent Members Having Lower Density and Lower Basis Weight Acquisition Zones", issued to Alemany et al. on May 30, 1989; U.S. Pat. No. 4,888,231 entitled "Absorbent Core Having A Dusting Layer" issued to Angstadt on Dec. 19, 1989; U.S. Pat. No. 5,137,537 entitled "Absorbent Structure Containing Individualized, Polycarboxylic Acid Crosslinked Wood Pulp Cellulose Fibers" which issued to Herron et al. on Aug. 11, 1992; U.S. Pat. No. 5,147,345 entitled "High Efficiency Absorbent Articles For Incontinence Management" issued to Young et al. on Sep. 15, 1992; U.S. Pat. No. 5,342,338 entitled "Disposable Absorbent Article For Low-Viscosity Fecal Material" issued to Roe on Aug. 30, 1994; U.S. Pat. No. 5,260,345 entitled "Absorbent Foam Materials For Aqueous Body Fluids and Absorbent Articles Containing Such Materials" issued to DesMarais et al. on Nov. 9, 1993; U.S. Pat. No. 5,387,207 entitled "Thin-Until-Wet Absorbent Foam Materials For Aqueous Body Fluids And Process For Making Same" issued to Dyer et al. on Feb. 7, 1995; and U.S. Pat. No. 5,625,222 entitled "Absorbent Foam Materials For Aqueous Fluids Made From high Internal Phase Emulsions Having Very High Water-To-Oil Ratios" issued to DesMarais et al. on Jul. 22, 1997. Each of these patents is incorporated herein by reference.

The diaper 20 may also comprise at least one elastic waist feature 34 that helps to provide improved fit and containment. The elastic waist feature 34 preferably extends at least longitudinally outwardly from at least one waist edge 62 of the absorbent core 28 and generally forms at least a portion of the end edge 52 of the diaper 20. Disposable diapers are often constructed so as to have two elastic waist features, one positioned in the first waist region 36 and one positioned in the second waist region 38. Further, while the elastic waist feature 34 or any of its constituent elements may comprise one or more separate elements affixed to the diaper 20, the elastic waist feature 34 may be constructed as an extension of other elements of the diaper 20, such as the backsheet 26, the topsheet 24, or both the backsheet 26 and the topsheet 24.

The elastic waist feature 34 may be constructed in a number of different configurations including those described in U.S. Pat. No. 4,515,595 issued to Kievit et al. on May 7, 1985; U.S. Pat. No. 4,710,189 issued to Lash on Dec. 1, 1987; U.S. Pat. No. 5,151,092 issued to Buell on Sep. 9, 1992; and U.S. Pat. No. 5,221,274 issued to Buell on Jun. 22, 1993. Other suitable waist configurations may include waistcap features such as those described in U.S. Pat. No. 5,026,364 issued to Robertson on Jun. 25, 1991 and U.S. Pat. No. 4,816,025 issued to Foreman on Mar. 28, 1989. All of the above mentioned references are incorporated herein by reference.

The diaper 20 may also include a fastening system 40. The fastening system 40 preferably comprises tape tabs and/or hook and loop fastening components, although any other known fastening means are generally acceptable. Some exemplary fastening systems are disclosed in U.S. Pat. No. 3,848,594 entitled "Tape Fastening System for Disposable Diaper" issued to Buell on Nov. 19, 1974; U.S. Pat. No. 4,662,875 entitled "Absorbent Article" issued to Hirotsu et al. on May 5, 1987; U.S. Pat. No. 4,846,815 entitled "Disposable Diaper Having An Improved Fastening Device" issued to Scripps on Jul. 11, 1989; U.S. Pat. No. 4,894,060 entitled "Disposable Diaper With Improved Hook Fastener Portion" issued to Nestegard on Jan. 16, 1990; U.S. Pat. No. 4,946,527 entitled "Pressure-Sensitive Adhesive Fastener And Method of Making Same" issued to Battrell on Aug. 7, 1990; and the herein before referenced U.S. Pat. No. 5,151,092 issued to Buell on Sep. 9, 1992; and U.S. Pat. No. 5,221,274 issued to Buell on Jun. 22, 1993. The fastening system may also provide a means for holding the article in a disposal configuration as disclosed in U.S. Pat. No. 4,963,140 issued to Robertson et al. on Oct. 16, 1990. Each of these patents is incorporated herein by reference. In alternative embodiments, opposing sides of the garment may be seamed or welded to form a pant. This allows the article to be used as a pull-on type diaper, such as a training pant.

The diaper 20 may also comprise side panels 30. The side panels 30 may be elastic or extensible to provide a more comfortable and contouring fit by initially conformably fitting the diaper 20 to the wearer and sustaining this fit throughout the time of wear well past when the diaper 20 has been loaded with exudates since the elasticized side panels 30 allow the sides of the diaper 20 to expand and contract.

While the diaper 20 of the present invention preferably has the side panels 30 disposed in the second waist region 38, the diaper 20 may be provided with side panels 30 disposed in the first waist region 36 or in both the first waist region 36 and the second waist region 38. The side panels 30 may be constructed in any suitable configurations. Examples of diapers with elasticized side panels are disclosed in U.S. Pat. No. 4,857,067, entitled "Disposable Diaper Having Shirred Ears" issued to Wood, et al. on Aug. 15, 1989; U.S. Pat. No. 4,381,781 issued to Sciaraffa, et al. on May 3, 1983; U.S. Pat. No. 4,938,753 issued to Van Gompel, et al. on Jul. 3, 1990; the herein before referenced U.S. Pat. No. 5,151,092 issued to Buell on Sep. 9, 1992; and U.S. Pat. No. 5,221,274 issued to Buell on Jun. 22, 1993; U.S. Pat. No. 5,669,897 issued to LaVon, et al. on Sep. 23, 1997 entitled "Absorbent Articles Providing Sustained Dynamic Fit"; U.S. patent application Ser. No. 08/915,471 entitled "Absorbent Article With Multi-Directional Extensible Side Panels" filed Aug. 20, 1997 in the names of Robles, et al.; each of which is incorporated herein by reference.

The diaper 20 preferably further includes leg cuffs 32 which provide improved containment of liquids and other body exudates. Leg cuffs may also be referred to as leg bands, side flaps, barrier cuffs, or elastic cuffs. U.S. Pat. No. 3,860,003 describes a disposable diaper which provides a contractible leg opening having a side flap and one or more elastic members to provide an elasticized leg cuff (a gasketing cuff). U.S. Pat. Nos. 4,808,178 and 4,909,803 issued to Aziz et al. on Feb. 28, 1989 and Mar. 20, 1990, respectively, describe disposable diapers having "stand-up" elasticized flaps (barrier cuffs) which improve the containment of the leg regions. U.S. Pat. Nos. 4,695,278 and 4,795,454 issued to Lawson on Sep. 22, 1987 and to Dragoo on Jan. 3, 1989, respectively, describe disposable diapers having dual cuffs, including gasketing cuffs and barrier cuffs. In some embodiments, it may be desirable to treat all or a portion of the leg cuffs with a lotion, as described above.

Embodiments of the present invention may also include pockets for receiving and containing waste, spacers which provide voids for waste, barriers for limiting the movement of waste in the article, compartments or voids which accept and contain waste materials deposited in the diaper, and the like, or any combinations thereof. Examples of pockets and spacers for use in absorbent products are described in U.S. Pat. No. 5,514,121 issued to Roe et al. on May 7, 1996, entitled "Diaper Having Expulsive Spacer"; U.S. Pat. No. 5,171,236 issued to Dreier et al on Dec. 15, 1992, entitled "Disposable Absorbent Article Having Core Spacers"; U.S. Pat. No. 5,397,318 issued to Dreier on Mar. 14, 1995, entitled "Absorbent Article Having A Pocket Cuff"; U.S. Pat. No. 5,540,671 issued to Dreier on Jul. 30, 1996, entitled "Absorbent Article Having A Pocket Cuff With An Apex"; and PCT Application WO 93/25172 published Dec. 3, 1993, entitled "Spacers For Use In Hygienic Absorbent Articles And Disposable Absorbent Articles Having Such Spacer"; and U.S. Pat. No. 5,306,266, entitled "Flexible Spacers For Use In Disposable Absorbent Articles", issued to Freeland on Apr. 26, 1994. Examples of compartments or voids are disclosed in U.S. Pat. No. 4,968,312, entitled "Disposable Fecal Compartmenting Diaper", issued to Khan on Nov. 6, 1990; U.S. Pat. No. 4,990,147, entitled "Absorbent Article With Elastic Liner For Waste Material Isolation", issued to Freeland on Feb. 5, 1991; U.S. Pat. No. 5,62,840, entitled "Disposable Diapers", issued to Holt et al on Nov. 5, 1991; and U.S. Pat. No. 5,269,755 entitled "Trisection Topsheets For Disposable Absorbent Articles And Disposable Absorbent Articles Having Such Trisection Topsheets", issued to Freeland et al on Dec. 14, 1993. Examples of suitable transverse barriers are described in U.S. Pat. No. 5,554,142 entitled "Absorbent Article Having Multiple Effective Height Transverse Partition" issued Sep. 10, 1996 in the name of Dreier et al.; PCT Patent WO 94/14395 entitled "Absorbent Article Having An Upstanding Transverse Partition" published Jul. 7, 1994 in the name of Freeland, et al.; and U.S. Pat. No. 5,653,703 Absorbent Article Having Angular Upstanding Transverse Partition, issued Aug. 5, 1997 to Roe, et al. All of the above-cited references are hereby incorporated by reference herein.

Figure 7:
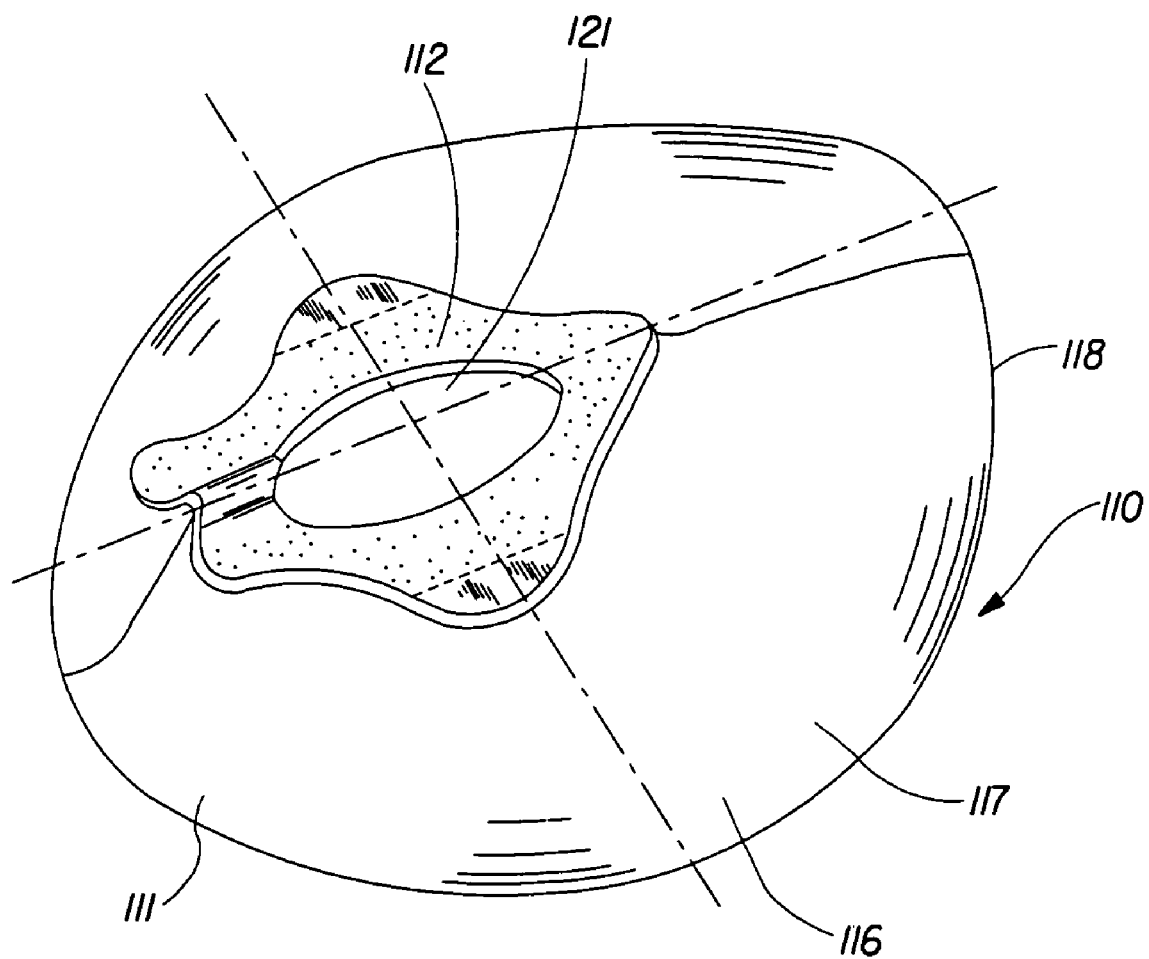
FIG. 7 is a perspective view of a waste bag embodiment of the present invention.
Figure 8:
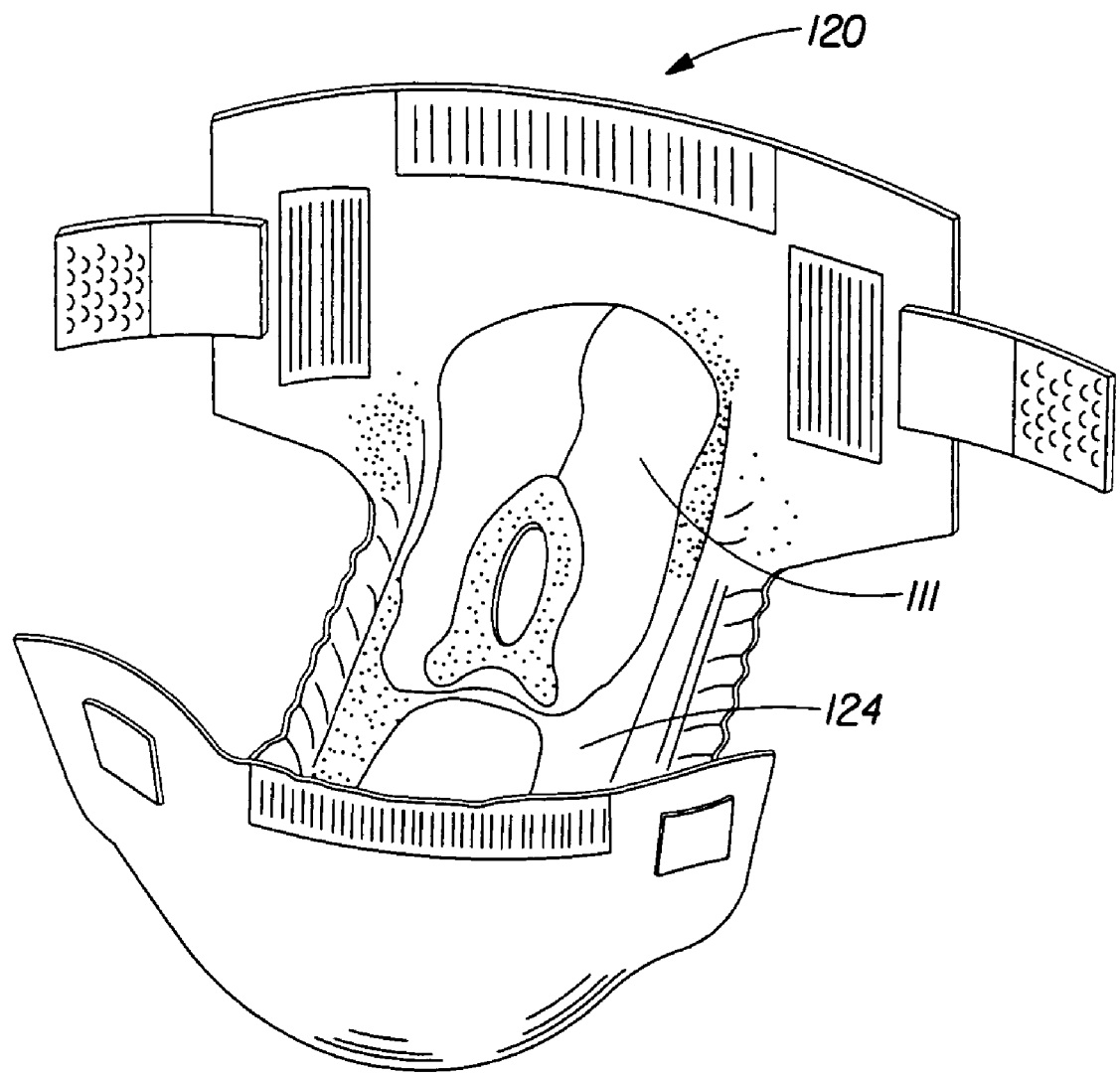
FIG. 8 is a perspective view of an absorbent article including a waste bag.

Embodiments of the present invention may also include a waste management device 110 such as is shown in FIG. 7. The waste management device 110 may include a waste bag 111 to collect feces, urine or both. The waste bag 111 may have an aperture 121 and a flange 112 surrounding the aperture for preferably adhesive attachment to the perianal area of a wearer. Further, the waste management device 110 has been found to be particularly useful and beneficial when used in conjunction with a garment, or diaper, preferably a disposable diaper. One example of an absorbent article, such as the diaper 120 including a waste bag 111 is shown in FIG. 8. If associated with a diaper 120 or other garment, the waste bag 111 may be disposed on or joined to any surface of the article. In one embodiment, the waste bag 111 is joined to the topsheet 124 of the diaper 120.

The waste bag 111 is preferably a flexible receptacle for the containment of excreted fecal matter or urine. Thus, the waste bag 111 is preferably liquid impermeable, and yet it may be breathable. Further, the waste bag 111 is designed of sufficient strength to withstand typical wearing conditions, such as sitting.

The waste bag 111 may comprise one or multiple layers. In one embodiment, the waste bag 111 may comprise three layers, preferably one film and two non-woven layers. The layers of the bag material may comprise any material, preferably so that the bag is liquid impervious. In a preferred embodiment of the present invention a laminate may be formed from a non-woven layer and a film.

Suitable film materials for any of the film layers preferably comprise a thermoplastic material. The thermoplastic material can may be vapor pervious or impervious and can be selected from among all types of hot-melt adhesives, polyolefins especially polyethylene, polypropylene, amorphous polyolefins, and the like; material containing meltable components comprising fibres or polymeric binders including natural fibres such as cellulose—wood pulp, cotton, jute, hemp; synthetic fibres such as fibreglass, rayon, polyester, polyolefin, acrylic, polyamid, aramid, polytetrafluroethylene metal, polyimide; binders such as bicomponent high melt/low melt polymer, copolymer polyester, polyvinyl chloride, polyvinyl acetate/chloride copolymer, copolymer polyamide, materials comprising blends wherein some of the constituent materials are not meltable; air and vapour permeable materials including microporous films such as those described above with respect to the backsheet and monolithic breathable materials such as HYTREL™ available from DuPont and Pebax™ available from ELF Atochem, France.

The waste bag 111 may have any shape or size. Preferred shapes include flat circular type bags, cone shaped bags, truncated cone shaped bags and pyramidal or truncated pyramidal shaped bags and flat T shaped bags. Further, the waste bag 111 may be provided from a unitary piece of material or a number of separate pieces of material which may be identical or different and which may be sealed at their respective peripheries.

The waste bag 111 may also contain absorbent material. The absorbent material may comprise any absorbent material which is capable of absorbing and retaining liquids. The absorbent material may comprise a wide variety of liquid-absorbent materials commonly used in disposable diapers and other absorbent articles. Some examples are described herein with respect to the absorbent core.

The waste bag 111 is provided with an aperture 121 whereby fecal matter or urine is received from the body prior to storage within the bag cavity. The aperture 121 is preferably surrounded by a flange 112 and may be provided in any shape or size, such as circular, oblong, heart shaped and may be symmetrical or asymmetrical, preferably the aperture has an oblong configuration either in the longitudinal or in the transversal direction. The flange may comprise projections designed to fit the perineal, genital and/or coccygeal area of the wearer.

The flange 112 should be made of soft, flexible and malleable material to allow easy placement of the flange 112 to the perianal or uro-genital area. Typical materials include nonwoven materials, wovens, open celled thermoplastic foams, closed-cell thermoplastic foams, composites of open celled foams and stretch nonwoven, and films.

The waste bag 111 preferably further comprises an attachment means to secure the device to the wearer. Such means may comprise straps and or a body-compatible pressure sensitive adhesive applied to the wearer facing portion of the waste bag 111 or the flange. Any skin-friendly water resistant pressure sensitive adhesive may be used to attach the device to the perianal or uro-genital area of the wearer, such as hydrocolloid adhesives and hydrogel adhesives. Particularly effective adhesives in providing the desired adhesive properties to secure the flange to the skin of the wearer at the sensitive perianal area, while allowing for relatively painless application and removal, are formed from crosslinking polymers with a plasticizer to form a 3-dimensional matrix.

The article 20 preferably also includes at least one biosensor 60. As used herein, the term "biosensor" is defined as a component comprising one or more biologically reactive means being adapted to detect one or more target pathogenic microorganisms or related biomolecules (e.g., an enzyme sensor, organella sensor, tissue sensor, microorganism sensor, immunosensor or electrochemical sensor), additionally having the capability to provide a signal of said detection to the wearer, caretaker, or an actuator. The term "biologically reactive" is defined as having the capability to selectively interact with, and preferably bind, target pathogenic microorganisms and/or related biomolecules as described herein. Generally, biosensors function by providing a means of specifically binding, and therefore detecting, a target biologically active analyte. In this way, the biosensor is highly selective, even when presented with a mixture of many chemical and biological entities, such as feces. Chemical sensors, on the other hand, which rely on chemically reactive means, generally do not have either the high selectivity or the amplification properties of biosensors and, therefore, are not well suited to detect biologically reactive analytes, especially when they are present in low concentrations and/or in a complex media such as bodily waste. Often the target biological analyte is a minor component of a complex mixture comprising a multiplicity of biological and other components. Thus, in many biosensor applications, detection of target analytes to the parts-per-billion, parts-per-trillion, or even lower levels is necessary. Accordingly, discrimination ratios of about $10^7$-$10^8$ or greater may be required for the biosensor to recognize the target biological analyte in a complex mixture.

The biosensor of the present invention comprises a bio-recognition element, or molecular recognition element, that provides the highly specific binding or detection selectivity for a particular analyte. The bio-recognition element, or system, may be a biologically derived material such as an enzyme or sequence of enzymes; an antibody; a membrane receptor protein; DNA; an organelle, a natural or synthetic cell membrane; an intact or partial viable or nonviable bacterial, plant or animal cell; or a piece of plant or mammalian tissues, and generally functions to interact specifically with a target biological analyte. The bio-recognition element is responsible for the selective recognition of the analyte and the physico-chemical signal that provides the basis for the output signal.

Biosensors may include biocatalytic biosensors, and bioaffinity biosensors. In biocatalytic biosensor embodiments, the bio-recognition element is "biocatalytic" and may comprise an enzyme, organelle, piece of plant or mammalian tissue, or whole cells, the selective binding sites "turn over" (i.e., can be used again during the detection process), resulting in a significant amplification of the input signal. Biocatalytic sensors such as these are generally useful for real-time, continuous sensing.

Bioaffinity sensors are generally applicable to bacteria, viruses, and toxins and include chemoreceptor-based biosensors and/or immunological sensors (i.e. immunosensors). Chemoreceptors are complex biomolecular macroassemblies responsible, in part, for a viable organism's ability to sense chemicals in its environment with high selectivity. Chemoreceptor-based biosensors comprise one or more natural or synthetic chemoreceptors associated with a means to provide a signal (visual, electrical, etc.) of the presence or concentration of a target biological analyte. In certain embodiments, the chemoreceptor may be associated with an electrode (i.e., an electrical transducer) so as to provide a detectable electrical signal. Chemoreceptors may include whole or partial nerve bundles (e.g., from antennae or other sensing organs) and/or whole or partial natural or synthetic cell membranes. On the other hand, the bio-recognition elements of immunosensors are generally antibodies. Antibodies are highly specific and can be made toward bacteria, viruses, fragments of microorganisms (e.g., bacterial cell walls, parasite eggs or portions thereof, etc.), and large biomolecules. Suitable antibodies may be monoclonal or polyclonal. In any case, bioaffinity biosensors are generally irreversible because the receptor sites of the biosensor become saturated when exposed to the target biological analyte.

In certain embodiments, biocatalytic bioaffinity biosensors may be combined, such as RNA/DNA probes or other high-affinity binding systems wherein the initial bio-recognition event is followed by biological amplification of the signal. For example, a specific bacteria may be detected by a biosensor comprising genetic material, such as DNA, as a bio-recognition element and PCR (i.e., polymerase chain reaction) amplification to detect small numbers of organisms, preferably less than or equal to about 500. Biocatalytic and bioaffinity biosensor systems are described in more detail in *Journal of Chromatography*, 510 (1990) 347-354 and in the Kirk-*Othmer Encyclopedia of Chemical Technology*, 4th ed. (1992), John Wiley & Sons, NY, the disclosure of which is incorporated by reference herein.

The biosensors of the present invention preferably detect biologically active analytes related to impending (i.e., future presentation of symptoms is likely) or current human systemic disease states, including, but not limited to, pathogenic bacteria, parasites (e.g., any stage of the life cycle, including eggs or portions thereof, cysts, or mature organisms), viruses, fungi such as *Candida albicans*, antibodies to pathogens, and/or microbially produced toxins. Additionally, the biosensor may target biologically active analytes related to impending or current localized health issues, such as stress proteins (e.g., cytokines) and IL-1α (interleukin 1-alpha) that may precede the clinical presentation of skin irritation or inflammation. In preferred embodiments, the biosensor functions as a proactive sensor, detecting and signaling the wearer or caretaker of the impending condition prior to the presentation of clinical symptoms. This allows time to administer prophylactic or remedial treatments to the wearer which can significantly reduce, if not prevent, the severity and duration of the symptoms. Further, the biosensor 60, by detecting the presence of a target biological analyte in the wearer's bodily waste (e.g., feces), may detect residual contamination on a surface, such as skin, in contact with the biosensor, and provide and appropriate signal.

The physico-chemical signal generated by the bio-recognition element or elements may be communicated visually to the wearer or caretaker (i.e., via a color change visible to the human eye). Other embodiments may produce optical signals, which may require other instrumentation to enhance the signal. These include fluorescence, bioluminescence, total internal reflectance resonance, surface plasmon resonance, Raman methods and other laser-based methods. Exemplary surface plasmon resonance biosensors which may comprise bioconjugate surfaces as bio-recognition elements are available as IBIS I and IBIS II from XanTec Analysensysteme of Muenster, Germany. Alternatively, the signal may be processed via an associated transducer which, for example, may produce an electrical signal (e.g., current, potential, inductance, or impedance) that may be displayed (e.g., on a readout such as an LED or LCD display) or which triggers an audible or tactile (e.g., vibration) signal or which may trigger an actuator, as described herein. The signal may be qualitative (e.g., indicating the presence of the target biological analyte) or quantitative (i.e., a measurement of the amount or concentration of the target biological analyte). In such embodiments, the transducer may optionally produce an optical, thermal or acoustic signal.

In any case, the signal may also be durable (i.e., stable and readable over a length of time typically at least of the same magnitude as the usage life of the article) or transient (i.e., registering a real-time measurement). Additionally, the signal may be transmitted to a remote indicator site (e.g., via a wire, or transmitter, such as an infrared or rf transmitter) including other locations within or on the article or remote devices. Further, the biosensor 60, or any of its components, may be adapted to detect and/or signal only concentrations of the target biological analyte above a predefined threshold level (e.g., in cases wherein the target biological analyte is normally present in the bodily waste or when the concentration of the analyte is below a known "danger" level).

As described above, the target analytes that the biosensors of the present invention are adapted to detect may be pathogenic microorganisms such as the pathogenic microorganisms implicated in human gastrointestinal diseases, especially those resulting in diarrhea. This type of pathogen is particularly important to monitor due to the number of children who become seriously ill or die each year from diarrheal diseases. It has been found that severe chronic diarrhea may result in weight loss and permanent physical and mental developmental retardation. A non-limiting list of pathogenic bacteria that the biosensor 60 may detect include any of the various pathogenic strains of *Escherichia coli* (commonly known as *E. coli*); Salmonella strains, including *S. typhi, S. paratyphi, S. enteriditis, S. typhimurium*, and *S. heidelberg;* Shigella strains such as *Shigella sonnei, Shigella flexneri, Shigella boydii*, and *Shigella dysenteriae; Vibrio cholerae; Mycobacterium tuberculosis; Yersinia enterocolitica; Aeromonas hydrophila; Plesiomonas shigelloides*; Campylobacter strains such as *C. jejuni* and *C. coli; Bacteroides fragilis*; and *Clostridia* strains, including *C. septicum, C. perfringens, C. botulinum*, and *C. difficile*. A non-limiting example of a commercially available biosensor adapted to detect *E. coli* is available from AndCare, Inc. of Durham, N.C., as test kit #4001. ABTECH, Scientific, Inc., of Yardley, Pa. offers "bioanalytical biotransducers", available as BB Au-1050.5-FD-X, which may be rendered biospecific (for microorganisms or other target biological analytes as described herein) by covalently immobilizing polypeptides, enzymes, antibodies, or DNA fragments to their surfaces. Other suitable microbial biosensors are described in U.S. Pat. No. 5,869,272 (gram negative organisms); U.S. Pat. No. 5,795,717 (Shigella); U.S. Pat. Nos. 5,830,341; 5,795,453; 5,354,661; 5,783,399; 5,840,488; 5,827,651; 5,723,330; and 5,496,700, all of which are incorporated herein by reference.

The target analytes that the biosensors of the present invention are adapted to detect may also be viruses. These may include diarrhea-inducing viruses such as rotavirus, or other viruses such as rhinovirus and human immunodeficiency virus (HIV). An exemplary biosensor adapted to detect HIV is described in U.S. Pat. Nos. 5,830,341 and 5,795,453, referenced above. The disclosure of each of these patents is incorporated by reference herein.

In alternative embodiments, the target analytes that the biosensors of the present invention are adapted to detect may also be parasites, especially those which inhabit the gastrointestinal tract during some point in their life-cycle. Such parasites may include protozoans, worms, and other gastrointestinal parasites. Other examples of parasites which may be detected include *entamoeba histolytica* (which cause amoebic dysentery), *trypana cruzi* (which causes Chagas disease), and *plasmodium falciparum*.

In yet other embodiments, the target analytes the biosensors of the present invention are adapted to detect may fungi such as Candida albicans. In addition to pathogenic bacteria, certain beneficial colonic bacteria may be detected and/or measured as a health indicator, such as Bifidobacteria and Lactobacillus strains.

The target analytes that the biosensors of the present invention are adapted to detect may also be proteins or antigens related to skin distress. Preferably, these analytes are detectable on or at the skin surface, preferably prior to the presentation of clinically observable skin irritation. These may include stress proteins such as cytokines, histamine, and other immune response factors including interleukins (such as IL-1α, IL-2, IL-3, IL-4, and IL-8) and interferons (including interferons a and g). Again, these are preferably detectable by the biosensor 60 prior to the onset of clinically observable redness, irritation, or dermatitis. Additionally, the biosensors of the present invention may be adapted to detect enzymes, or other biological factors, implicated in skin irritation (e.g., diaper dermatitis), including tryspin, chymotrypsin, and lipase.

The biosensors of the present invention may also comprise bio-recognition systems, including enzymes or binding proteins such as antibodies immobilized onto the surface of physico-chemical transducers. For example, a specific strain of bacteria may be detected via biosensors employing antibodies raised against that bacterial strain. Alternatively, a target bacteria may be detected by a bio-recognition element (including antibodies and synthetic or natural molecular receptors) specific to extracellular products of the target bacteria, such as toxins produced by that strain (e.g., *E. coli*). Exemplary enzyme electrodes that may be used to detect phenols (e.g. in urine or feces) include tyrosinase based electrodes or polyphenol oxidase enzyme electrodes described in U.S. Pat. No. 5,676,820 entitled "Remote Electrochemical Sensor," issued to Joseph Wang et al. on Oct. 14, 1997 and U.S. Pat. No. 5,091,299 entitled "An Enzyme Electrode For Use In Organic Solvents," issued to Anthony P. F. Turner et al. on Feb. 25, 1992, respectively. Both of these patents are incorporated by reference herein.

In any of the foregoing examples, the specific microorganism may be directly detected or may be detected by binding a toxin, enzyme, or other protein produced by the organism or an antibody, such as a monoclonal antibody, specific to the organism. Exemplary biosensors adapted to detect proteolytic enzymes described in U.S. Pat. No. 5,607,567 and toxins in U.S. Pat. Nos. 5,496,452; 5,521,101; and 5,567,301.

The biosensor 60 of the present invention may comprise one or more "proactive sensors". This is especially useful in embodiments where the detection of the target biologically reactive analyte precedes the onset of clinically observable health symptoms. As used in this application, the term "proactive sensor" refers to a sensor that is capable of detecting changes or signals on the body of the wearer (i.e., skin) or in the waste, i.e., inputs, that directly relate or, at a minimum, correlate to the occurrence of an impending or potential health or skin related even. Proactive sensors may respond to one or more specific inputs as described above.

A proactive sensor 60 may detect an impending event or detect a parameter that directly relates, or at a minimum correlates to the occurrence of an impending event, particularly a systemic or skin health event or condition (i.e., the presentation of clinically observable indications or symptoms). An impending event that may be detected or predicted by a proactive sensor 60 of the present invention may include diarrheal disease, skin irritation or rash (including candidiasis), and/or other types of illness or medical conditions of the wearer such as a parasitic infestation. The detected biological analyte may be one or more steps removed from the actual presentation of clinical symptoms. For example, the biosensor may detect potential precursors to the above conditions (e.g., fecal contamination of the skin that may precede the elicitation of stress proteins which may, in turn, precede clinically observable skin irritation. A parameter that correlates to an event is any measurable input, signal such as one or more of the potential inputs listed above, that correlates with the occurrence of the event within the frame of reference of the system (i.e., a signal caused by the waste or the wearer). Proactive sensors 60 in an article may measure one or more different inputs in order to predict an event. For example, the proactive sensor 60 may monitor for *Candida albicans* in the feces and residual colonic bacteria on the skin (i.e., detecting residual contamination) both of which are signals that may precede skin irritation.

In biosensor embodiments wherein the bio-recognition element does not produce an easily visible signal (e.g., a color change), the biosensor 60 may include a transducer in communication with the bio-recognition element in order to convert the physico chemical signal from the bio-recognition element into a usable signal to the wearer, caretaker, or component of the article (e.g., and actuator). Exemplary transducers may include electrochemical transducers (including potentiometric, amperometric, and conductimetric transducers), optical transducers (including fluorescence, bioluminescence, total internal reflective resonance, and surface plasmon resonance), thermal transducers, and acoustic transducers, as known in the art. A power source, such as a miniature 3 volt watch battery or printed thin film lithium battery, may be connected with the biosensor 60 to provide any required power.

The effectiveness of the biosensors of the present invention may be measured with the Response Factor Test described in the Test Method section below. The Response Factor describes the ratio of the response of the biosensor when exposed to fecal test material compared to the response of the biosensor when exposed to physiological saline solution and is useful in assessing the sensitivity of the biosensor for biologically active analytes expected to be found preferentially in feces versus urine. The biosensors of the present invention preferably have a response factor of at least 2, 3, or 5, more preferably at least 10, and even more preferably at least 20 when exposed to fecal test material in aqueous solution or test urine having a concentration of 1 gram of fecal test material per 1 gram of physiological saline solution. (Physiological saline solution is used here to represent the background input signal which is present in most natural environments such as aqueous body fluids.) Such biosensors are able to clearly distinguish between the presence of fecal material and the presence of physiological saline solution with respect to a target biologically active analyte specific to feces.

One way to detect feces is to detect skatole, a substance commonly found in fecal material. It has been found that the skatole concentration in feces is about 180 microgram per gram of fecal material whereas the skatole level in urine has been found to be substantially lower. Skatole is generally a product of microbiological degradation that originates from the catabolism of tryptophane in the intestinal system.

In one preferred embodiment of a skatole detecting biosensor, the biosensor comprises genetically engineered microorganisms which assimilate skatole and or other substances. The assimilation of skatole specific substances can be measured, for example, via the oxygen consumption during the assimilation process. Microorganisms suitable for detecting skatole include *Acinetobacter baumannii* T0136 (FERM P-12891, Japanese patent publication JP05304947), and *Bacillus sp* T0141 (FREM P-12914, disclosed in Japanese patent publication JP05304948). Suitable biosensors including such microorganisms are commercially available for example from Institut für Chemo-und Biosensorik of Münster, Germany, under the designation Mikrobielle Sensoren.

If microorganisms are incorporated into a biosensor, they may be immobilized in the biosensor by techniques known in the art such as entrapment, adsorption, crosslinking, encapsulation, covalent attachment, any combination thereof, or the like. Further, the immobilization can be carried out on many different substrates such as known the art. In certain preferred embodiments, the immobilization substrate may be selected from the group of polymer based materials, hydrogels, tissues, nonwoven materials, woven materials.

In certain embodiments, the sensor 60, including any biosensor embodiments, may comprise, be disposed on, or be operatively associated with a microchip, such as a silicon chip, MEMs (i.e., micro electromechanical system) device, or an integrated circuit. Microchip-based biosensors may be known as "biochips". Regardless of the type of sensor, the microchip may comprise a multiplicity of sensor components having similar or different sensitivities, kinetics, and/or target analytes (i.e., markers) in an array adapted to detect differing levels or combinations of said analyte(s). Further, each sensor in such an array may provide a different type of signal, including those types disclosed herein, and may be associated with different actuators and/or controllers. Also, each sensor in an array may operate independently or in association with (e.g., in parallel, combination, or series) any number of other sensors in the array.

The biosensor 60 may be disposed in and/or operatively connected to any portion of a disposable article that will be exposed to the input that the biosensor is designed to detect. For the purposes of the present invention, the term "operatively connected" refers to a means of communication such that the biosensor 60 may signal some portion of the article 20 when the biosensor 60 detects an input. The biosensor 60 may be separate from and operatively connected to another portion of the biosensor 60, another biosensor 60, an actuator, a controller or some other portion or component of the article 20. "Operatively connected" may, for example, include a means of communication such as an electrical connection via a conductive wire or member, via a transmitted signal such as radio frequency, infrared or another transmitted frequency communication. Alternatively, the biosensor 60 may be operatively connected via a mechanical connection such as a pneumatic or a hydraulic connection.

In disposable article embodiments (e.g., diaper 20 of FIG. 1), the biosensor 60 may be located in the front waist region 36, the rear waist region 38 or the crotch region 37 of article 20, and may be integral with, disposed adjacent to, joined to, or comprise a portion of the chassis 22, the topsheet 24, the backsheet 26, the absorbent core 28, side panels 30, leg cuffs 32, a waist feature 34, a fastening system 40, the longitudinal 50 or end 52 edges, etc. In certain preferred embodiments wherein the target biological analyte is associated with bodily waste, the biosensor to 60 may be disposed in the crotch region of the article 20 so as to maximize the probability of the bodily waste contacting the biosensor 60. In other preferred embodiments wherein the biosensor is adapted to detect or measure a target biological agent on the wearer's skin, the biosensor 60 may be disposed on the topsheet, cuff, a waist feature, a feces receiving pocket, spacer, or any other portion of the article that will contact the wearer's skin during the usage process. In certain embodiments, the biosensor may also be associated with the lotion or other skin care composition within the article.

The biosensor 60 may be integral with the article 20, or may be installed by the caretaker or the wearer. The biosensor during the course of wearing the article may also become at least partially detached from the article and may be adhered to the wearer's skin. The biosensor may be affixed, permanently or detachably (e.g., via a mechanical fastening system like Velcro™ or a water soluble adhesive) to a support structure, including adhesive tapes, cellulosic or synthetic webs, nonwoven highlofts, films, scrims, foams, and the like. Further, the biosensor 60 may be completely contained within the article such as article 20 or may have a receiving portion located in the article such that it will come into contact with the desired input and another portion such as a transmitting portion located either in the article or outside the article. The biosensor 60 may be external to the article 20 yet operatively connected to some portion of the article 20 such that the biosensor 60 may detect an input external to the article 20 and provide a signal to a controller and/or an actuator. In some embodiments, the biosensor may be separate from the article, e.g., separately applied to some portion of the wearer via adhesive or other means as known in the art, and/or may have one or more components separate from the article.

In some embodiments, a wiping means or element may be provided to allow the wearer or caretaker to clean sufficient bodily waste from the biosensor 60 to allow a visual assessment or reading of the signal (especially for biosensor embodiments that provide such a signal). The wiping element may include a web (cellulosic or synthetic), nonwoven highloft, film, foam, rigid or semi-rigid squeegee like element, and the like disposed in the article and adapted such that the element may be used to clean the biosensor display. The wiping element may be at least partially affixed the to a component of the article, such as a topsheet, in proximity to the biosensor 60 by any known means in the art. The wiping means may optionally comprise water or any other known cleaning aid to facilitate cleaning of the wearer or the biosensor display.

In certain preferred embodiments, the article 20 also may comprise an actuator. As used in this application, the term "actuator" refers to a device that comprises "potential" and a means of transforming that potential to perform or activate a "responsive function." The potential of the actuator may comprise either stored or potential energy or stored material. The actuator thus may perform or activate a responsive function by transforming potential energy to kinetic energy or by releasing or delivering a stored material. A "responsive function" is defined for the purposes of the present invention as a function performed upon the bodily waste, the wearer, the article, or a component or components thereof, or a signal to the wearer or the caretaker. A component of bodily waste may include, for example, moisture, electrolytes, enzymes, volatile gases, bacteria, blood, etc. A component of the wearer may also include skin, genitalia, the anus, the anal sphincter muscle, etc. A component of the article may also include leg cuffs, waist cuffs or other waste barriers and/or containment components, side panels, ears, a chassis, an absorbent core, an acquisition component, a fastening system, the longitudinal or end edges, etc. Potential energy may be stored as mechanical, electrical, chemical or thermal energy. "Kinetic energy" as used in this application refers to the capacity to do work or to perform a responsive function as described above (e.g., expansion of a compressed device, rotation of a twisted device, a gel that moves as it changes phases, coating or treatment of skin or feces, inhibition of an enzyme, adjustment of pH, etc.).

Triggering the creation of a three dimensional structure to capture waste, for example, involves responsive functions performed on a component of the article and, ultimately, on the waste. Capturing waste, wiping the skin of the wearer or treating the skin with a skin care composition, antimicrobial agent, antifungal agent or enzyme inhibitor, for example, are responsive functions performed on the waste and/or the wearer. Adjusting the article's geometry (in one, two or three dimensions) or physical properties (e.g., bending modulus, geometry, etc.) are examples of responsive functions, which may be performed on the article. Signaling a caretaker and/or the wearer that an event has occurred, or is about to occur, is also considered a responsive function for the purposes of the present invention. The signal may be visual, auditory, tactile, electrical, chemical, or biological. An actuator of a disposable article may, for example, release or deliver a deodorant, enzyme inhibitor, antimicrobial agent, antifungal agent, skin care composition or pH control agent; capture, wipe, cover, trap, immobilize, seal, pump, or store bodily waste; or trigger the release or creation of a structure or element designed to perform one or more of these functions or any other responsive function upon the waste, wearer, article, or a component thereof.

The actuator of the present invention may release potential energy to perform or activate a responsive function upon the waste, the wearer, the article, or a component thereof. The release of potential energy may transform mechanical, electrical, chemical or thermal potential energy into mechanical, electrical or chemical kinetic energy to perform the responsive function. Actuators may be triggered by a threshold level of an input to release potential energy to perform a responsive function or may respond continuously to an input as described below. For example, a compressed foam has stored compressive mechanical potential energy and may provide mechanical kinetic energy when it is released. A twisted foam has stored torsional mechanical potential energy that may provide mechanical kinetic energy, i.e., rotation, when it is released. In addition, stored chemical, electrical or thermal energy may be used to release electrical, mechanical, chemical or thermal kinetic energy. The actuator of a disposable article, for example, may include one or more of the following: stored lotion, anti-fungal or antimicrobial agents, feces modification agents, enzyme inhibitors, pH buffers, dyes, pressurized gas, a compressed foam, a twisted foam, a pump, a closed system liquid transport member, an electrically sensitive gel, a pH sensitive gel, a salt concentration gel, etc. Potential energy may be stored in any manner sufficient to maintain or restrain it until it is required. Suitable means for maintaining and/or restraining such energy include batteries and/or capacitors, elastically, torsionally, compressively tensioned materials or structures in the form of unreacted reagents, and materials capable of performing physical or chemical functions (e.g., absorbents, emollients, pH buffers, enzyme inhibitors, feces modification agents; compressed gases, etc.).

Alternatively, the actuator of the present invention may comprise a quantity of a stored material that has the capacity to perform or activate a responsive function upon the waste, the wearer, the article, or any component or components thereof. In one embodiment, for example, the actuator may release or deliver a stored material that performs a responsive function. In this embodiment, the actuator may be triggered by a threshold level of an input to discontinuously release or deliver the stored material at a given time or may release or deliver the material continuously. The actuator may, for example, include stored lotion, skin care compositions, anti-fungal or antimicrobial agents, feces modification agents, enzyme inhibitors, pH buffers, dyes, etc. In certain preferred embodiments, the material may be delivered by an actuator such as an expanding resilient material, a released high pressure gas, etc.

Figure 2:
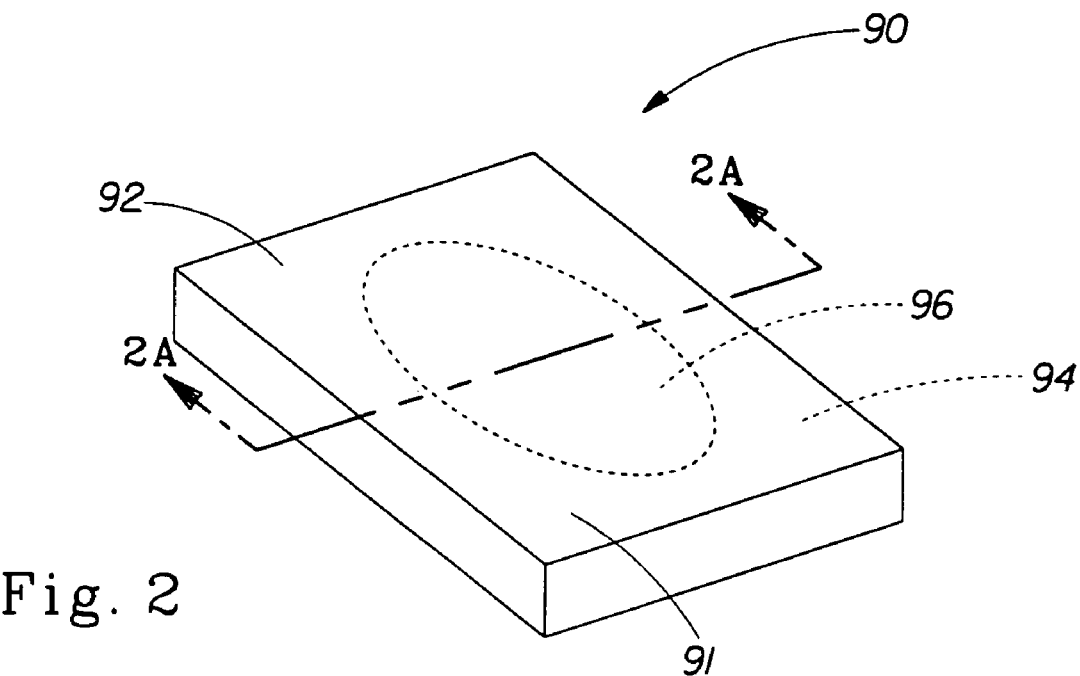
FIG. 2 shows a perspective view of a bodily waste isolation device of the present invention in a compressed state before activation.
Figure 2A:
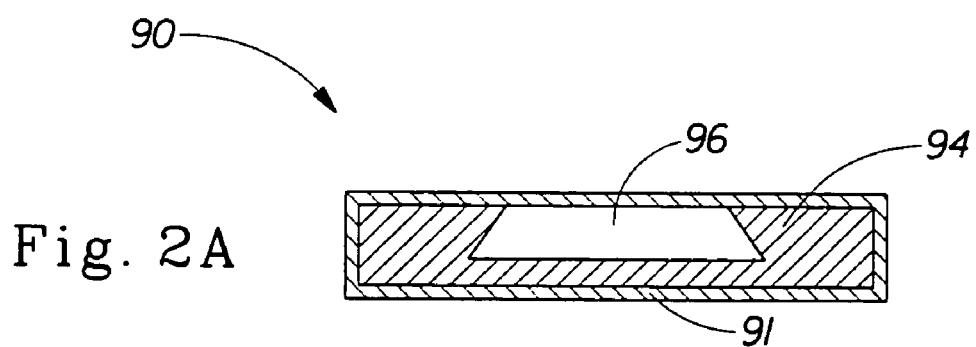
FIG. 2A shows a sectional view taken along line 2A-2A of FIG. 2.

FIGS. 2 and 2A illustrate an actuator 90 comprising a compressed resilient material 94, such as a foam, sealed under at least a partial vacuum within a pressure differentiation device 91. A pressure differentiation device, as used herein, is any device or structure that can maintain a resilient material in a compressed state (e.g., can store energy by providing a constraining pressure on the compressed resilient material 94). A "compressed state" is defined as the condition in which a material is maintained at a smaller volume than the material would have if unconstrained and under zero applied pressure. With respect to resilient materials, a compressed state may generally be achieved by applying a pressure to a surface of the material or via any other means known in the art. The pressure differentiation device may, for example, comprise a vacuum sealed bag or tensioned materials, such as elastic or inelastic bands or strands, strips, films, nonwoven, scrims, or foams, that constrain a resilient material. Preferably, the compression of the resilient material maintained by the pressure differentiation device 91 may be at least partially reduced (i.e., the compressed resilient material 94 may at least partially expand) via a trigger mechanism. A trigger mechanism is any element or device, such as a sensor, actuator, or combination thereof, that responds to an input to effect the equalization of pressure in the pressure differentiation device 91 and allow the compressed resilient material 94 to at least partially expand. Upon release of the compressed material, such as when a target biologically active analyte is detected, the compressed resilient material may expand and deliver the stored material. In some embodiments, it may be advantageous for the actuator 90 to comprise a void space 96.

The resilient material 94 may comprise any resilient material, including but not limited to, an EVA foam such as the ones available from Foamex Corporation of Eddystone, Pennsylvania identified as SIF/210PPI or Aquazone 80A foam, or from Sentinel Products Corporation of Hyannis, Mass. identified as MC1900 EVA 2 lb/ft$^3$, or a HIPE foam as described in U.S. Pat. No. 5,260,345 entitled "Absorbent Foam Materials For Aqueous Body Fluids and Absorbent Articles Containing Such Materials" issued to DesMarais et al. on Nov. 9, 1993; U.S. Pat. No. 5,387,207 entitled "Thin-Until-Wet Absorbent Foam Materials For Aqueous Body Fluids And Process For Making Same" issued to Dyer et al. on Feb. 7, 1995; and U.S. Pat. No. 5,625,222 entitled "Absorbent Foam Materials For Aqueous Fluids Made From high Internal Phase Emulsions Having Very High Water-To-Oil Ratios" issued to DesMarais et al. on Jul. 22, 1997. (Each of the patents identified above is incorporated by reference herein.)

In some embodiments of the present invention, the pressure differentiation device 91 may comprise a bag, such as soluble bag 92. The soluble bag 92 may be soluble in the presence of one or more different types of input, such as water, urine, fecal enzymes, a pH level, etc., and may have physical and/or chemical characteristics (e.g., thickness) that may be designed to set a threshold level of that input required to dissolve the bag. The soluble bag may, for example, comprise a plastic film that is soluble to water such as PVA films supplied by Chris-Craft Industrial Products, Inc. of South Holland, Ill. as MONOSOL M7031, M7030, M8630, M8534, or E6030 film, or H. B. Fuller Company of St. Paul, Minn. as HL 1636 or HL 1669-X. The film thickness, for example, may also be modified to provide a desired activation. The film used may, for example, also have a thickness in the range from about 0.0005 to about 0.0015 inches. An HL 1636 film having a thickness of about 0.001 inches, for example, will activate with a moisture content of about 0.049 grams per square inch.

The actuator may alternatively comprise an electrically sensitive gel. Electrically sensitive gels are polymeric gel networks that, when at least partially swollen with water, change volume and/or geometry under the application of an electric current or field. For example, certain partially ionized polyacrylamide gels will undergo anisotropic contraction of about 50% under weak electric fields (e.g., 0.5 volts/cm) when immersed in acetone and water. Alternative electrically sensitive gels may undergo electrically induced bending in the presence of water and a surfactant or may undergo an oscillating wave motion when subjected to an oscillating electric field. It is believed that local shrinkage may be induced in a portion of the gel, e.g., one side of a gel element, by concentrating positively charged surfactant molecules on the negatively charged gel polymer in an electric field. Changing the intensity and/or the polarity of the field induces a movement in the gel as one side decreases in length (e.g., a gel formed in a strip may curl). Electrically sensitive gels may comprise variable geometries such as rectangular, circular, reticulated grid, etc. patterns in order to provide a valve to release a material, allow a bodily waste to flow through, prevent a bodily waste from flowing through, encapsulate a bodily waste, etc. as they change volume and/or geometry. An electrically sensitive gel formed in a strip, for example, may be bent to provide an available void space for when electrical activity in the external anal sphincter muscle predictive of defecation or urination is detected.

Figure 5A:
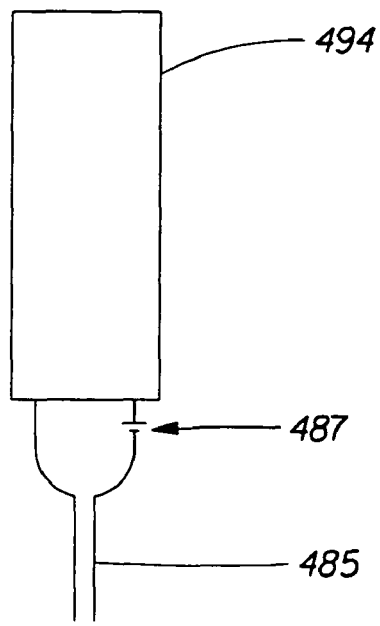
FIGS. 5A and 5B show an embodiment of a responsive system of the present invention including an electrically sensitive gel.
Figure 5B:
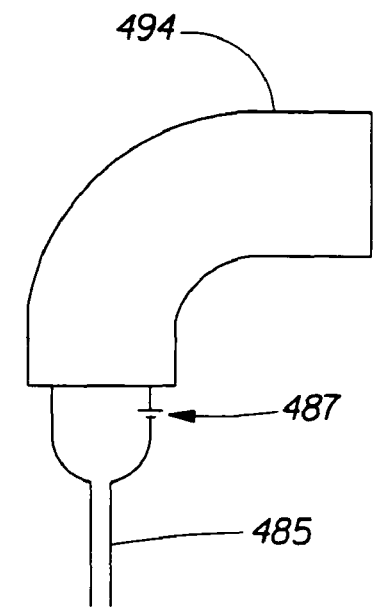
Figure 6A:
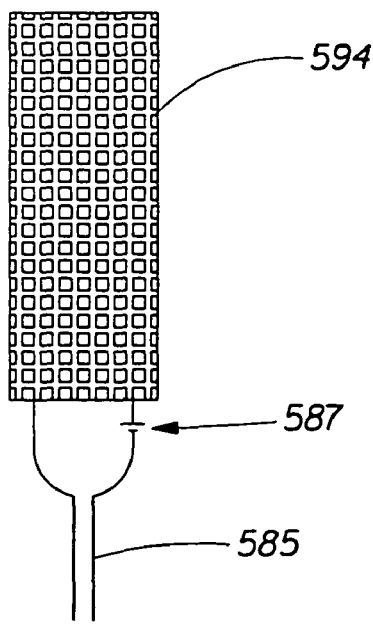
FIGS. 6A, 6B and 6C show another embodiment of a responsive system of the present invention including an electrically sensitive gel.
Figure 6B:
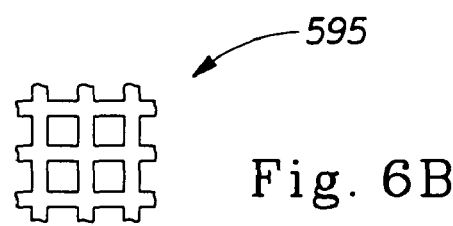
Figure 6C:
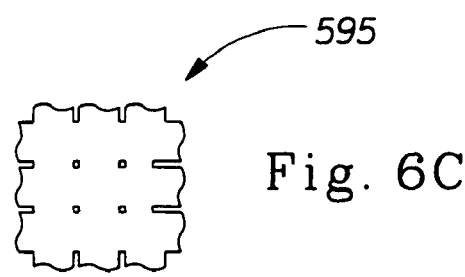

In FIGS. 5A and 5B, for example, a strip of electrically sensitive gel 494 is shown in a circuit in which fecal moisture may bridge the contacts 485 and allow current to flow to the electrically sensitive gel either bending or straightening the strip. Alternatively, an electrically sensitive gel 594 formed in a reticulated grid pattern 595, such as shown in FIGS. 6A, 6B and 6C, may be electrically induced to swell or shrink when an imminent urination is detected to form a valve that allows and/or prevents urine flow to another portion of the article 20. FIG. 6A, for example, shows a circuit including a reticulated grid pattern of an electrically sensitive gel. FIGS. 6B and 6C further show a microscopic view of the grid in a shrunk and in a swelled configuration, respectively. An exemplary material is a weakly cross-linked PAMPs gel (poly(acrylamido-2-methyl propane) sulphonic acid). This type of gel may perform various functions such as applying or delivering a chemical feces treatment agent. Other exemplary electrically sensitive gels are described in U.S. Pat. No. 5,100,933 issued to Tanaka on Mar. 31, 1990 and WO 9202005, both of which are incorporated by reference herein. Alternatively, pH sensitive gels or salt concentration sensitive gels that change volume and/or geometry at specific pH or salt concentrations, respectively, may be used as an actuator of the present invention.

The actuator may be disposed in and/or operatively connected to any portion of disposable article that will allow the actuator to perform a responsive function upon the bodily waste, the wearer, the article, or a component thereof. In article 20, for example, the actuator may be located in the front waist region 36, the rear waist region 38 or the crotch region 37 of article 20, and may be integral with, disposed adjacent to or joined to a component of the chassis 22, the topsheet 24, the backsheet 26, the absorbent core 28, side panels 30, leg cuffs 32, a waist feature 34, a fastening system 40, the longitudinal 50 or end 52 edges, etc. The actuator may also be completely contained within the article such as article 20, may have a portion located in the article and a portion located outside the article 20, or may be completely external to the article 20. An actuator or a portion of an actuator may be operatively connected to one or more biosensors 60, one or more controllers 80, another portion of the actuator or another portion of the article 20. Further, the actuator may be integral with the article 20, or may be installed by the caretaker or the wearer.

The article 20 may also include a controller. A "controller" is defined for the purposes of this application as a device that receives an input from a biosensor and determines if one or more actions are to be taken. The controller may receive a signal from the biosensor 60 and direct the actuator to perform a responsive function upon the bodily waste, the wearer, the article or a component thereof. Alternatively, the actuator may receive the signal directly from the biosensor 60 and perform a responsive function upon the wearer, the waste, the article or a component thereof. The controller may include materials that undergo chemical or physical change, may be a chemical, mechanical or electrical device that processes information from a biosensor, etc. The controller may include a transducer comprising a polylayer Langmuir-Blodgett film, wherein one or more layers includes a bio-recognition element. Upon contact with water, Langmuir-Blodgett films are known to spontaneously reorganize, resulting in regions with more layers than the original film and other regions having fewer layers. This reorganization may expose the bio-recognition element to the environment preferentially in the presence of water, such as in bodily waste, which may contain the target biological analyte. Thus, the number of false positives can be reduced and the shelf-life of the biosensor can be extended. Alternatively, an electrical controller that receives signals such as electrical potential from an electrochemical biosensor may receive and monitor multiple electrical signals and may repeatedly trigger the actuator. The controller may be integral with the biosensor component, integral with the actuator component, or a separate component of the system.

The controller may be disposed in and/or operatively connected to any portion of a disposable article that will allow the controller to receive a signal from the biosensor 60 and to provide a signal to the actuator. In article 20, for example, the controller may be located in the front waist region 36, the rear waist region 38 or the crotch region 37 of article 20, and may be integral with, disposed adjacent to or joined to the chassis 22, or a component of the topsheet 24, the backsheet 26, the absorbent core 28, side panels 30, leg cuffs 32, a waist feature 34, a fastening system 40, the longitudinal 50 or end 52 edges, etc. The controller may be integral with the article 20, or may be installed by the caretaker or the wearer. The controller may be completely contained within the article such as article 20, may have a portion located in the article and a portion located outside the article, or may be located completely outside the article 20. The controller or a portion of a controller may be operatively connected to one or more biosensors 60, one or more actuators 90, another portion of the controller or another portion of the article 20. The controller, for example, may receive a signal from the biosensor 60 and provide a signal to the actuator, e.g., by a radio frequency (rf) transmission.

Although distinct structural elements may perform the biosensor 60, actuator and controller functions, the biosensor 60, actuator and/or controller functions of the present invention need not be performed by distinct structural elements. The biosensor 60 and controller functions, for example, may be performed by the same structural element.

A "responsive system" is defined for the purposes of this application as a system that includes a biosensor 60 and an actuator that acts upon the bodily waste, the wearer, the article, or a component or components thereof when the biosensor 60 detects the appropriate triggering input. Upon sensing a given input parameter, the actuator affects the release of stored energy or the release or delivery of stored material to perform a responsive function. For example, when a proactive biosensor 60 including a transducer detects an impending event, the transducer provides a signal to the actuator affecting the release of stored energy. By detecting an input signal prior to the impending event, a responsive system in the article may be triggered to prepare for the event or to signal the caregiver or the wearer of the impending event. This allows construction of articles in which the waste-management or treating technology is initially "hidden" or unobtrusive, but which is available at, or just before, the moment of need and/or in which the article may provide the caregiver or the wearer the opportunity to prepare for an event in advance (e.g., administer a prohylactic treatment to the wearer in the event of detected pathogenic microorganisms or residual fecal contamination). Regardless of the specific input, the biosensor 60 in these embodiments may trigger an actuator to perform an action on the article, the wearer or the environment to prepare for the occurrence of the event or provide a signal to the caregiver that the impending event is about to occur. If the biosensor 60 comprises a sensing system, one actuator may be triggered by different biosensors and/or signals, or different actuators may be triggered by different biosensors and/or signals. Alternatively, one biosensor and/or signal may trigger multiple actuators.

A responsive system may respond in either a "continuous" or a "discontinuous" manner. As used in this application, a "continuous responsive system" refers to a responsive system in which the output is quantitatively dependent upon the quantity of the input, i.e., continuously increasing quantities of the input are required to affect continuously increasing quantities of the output, or where the output of the responsive system comprises a passive release of a stored material. A super absorbent polymer placed in an absorbent core of an article, for example, provides a continuous response in which the output is quantitatively dependent upon the quantity of the input, i.e., as increasing quantities of liquid waste contact the super absorbent polymer, an increasing amount of the polymer contains that liquid until the capacity of the polymer is exhausted. A stoichiometric chemical reaction is another example of a system having a continuous response to increasing output. In the reaction A+excess B→C, for example, the amount of excess B converted to C is stoichiometrically and, therefore "continuously," related to the amount of A available in the system.

Figure 3A:
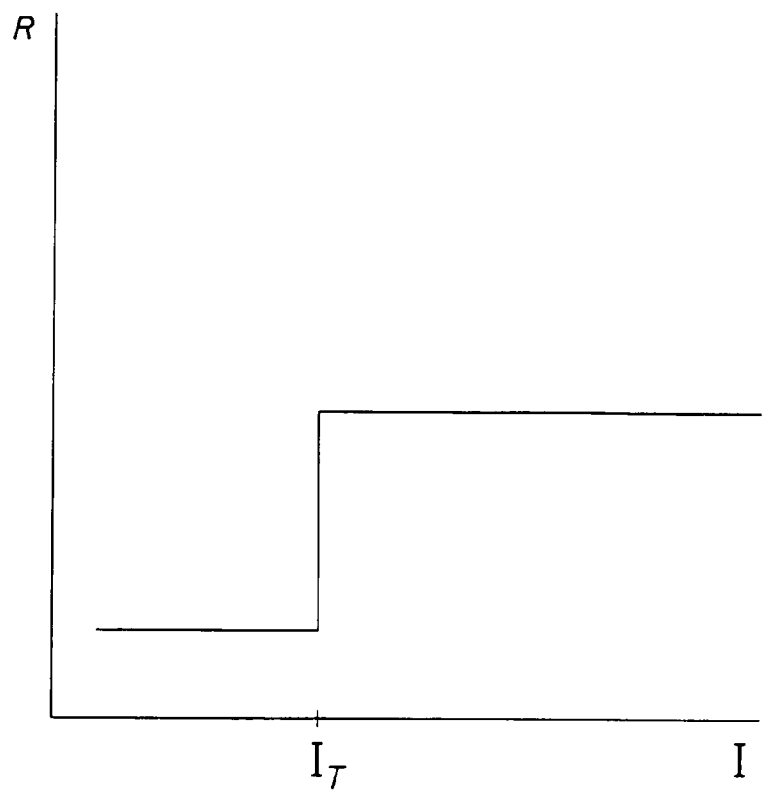
FIG. 3A shows an ideal output function of a discontinuous responsive system of the present invention having a single threshold level.

A "discontinuous responsive system" of the present invention, however, refers to a responsive system that has an output function that is essentially independent of the quantity of the input beyond a threshold level. For example, when one or more threshold levels of a given input are met, the responsive system may release all or a pre-designated portion of its stored energy or deliver, i.e., actively transport, all or a pre-designated portion of its stored material to perform a specific responsive function. In an ideal embodiment of the present invention, the output function, f(x), includes a "step" function as shown in FIG. 3A. In this embodiment, the rate of change in the output with increasing levels of input (d(output)/d (input)), i.e., the slope or first derivative f'(x) of the output function f(x), is preferably essentially zero when the amount of input is above or below the threshold level. At the threshold level, however, the d(output)/d(input) rate of change preferably approaches infinity. Thus, in the ideal discontinuous response, the limit of the function f(x−ε) as ε→0 is not equal to the limit of the function f(x+ε) as ε→0, i.e., $$\lim_{\varepsilon \to 0} f(x-\varepsilon) \ne \lim_{\varepsilon \to 0} f(x+\varepsilon).$$

Figure 4A:
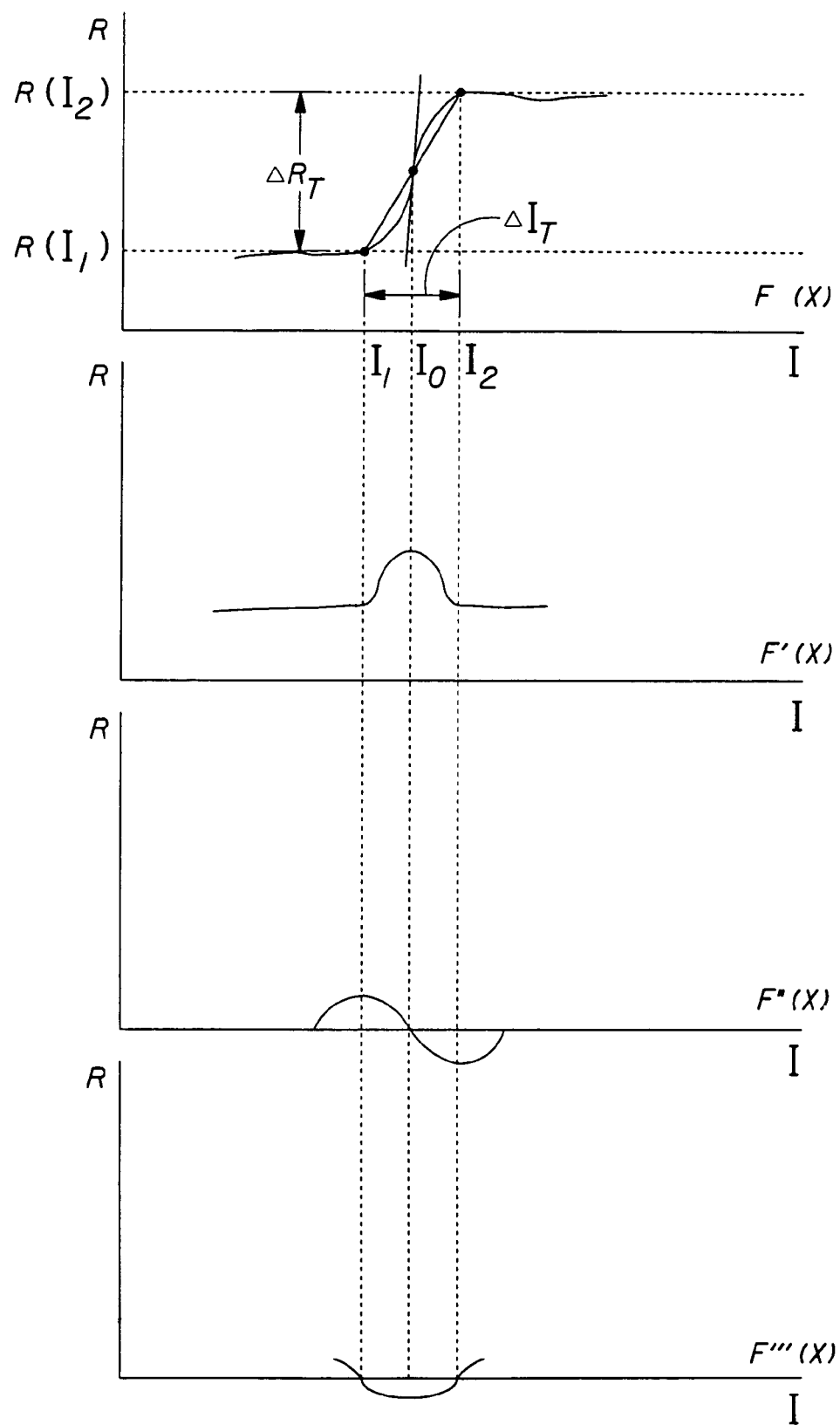
FIG. 4A shows an exemplary output function of a discontinuous responsive system of the present invention along with the first, second and third derivatives of the output function.

The present invention, however, recognizes that in the physical world an ideal instantaneous step change at the threshold level is not necessary and may not even be possible in many instances. In a preferred embodiment, it is only necessary that the output function have a virtual step change with very little change in the input at or around the threshold level of the input. Thus, the present invention contemplates a discontinuous responsive system of the present invention having an output function that responds in a sufficiently discontinuous manner in the transition region such that the output function has at least a minimum relative degree of steepness in the transition region. While not wishing to be limited to a particular method of describing or modeling a discontinuous system, in a preferred method of determining whether a given output function performs in a sufficiently discontinuous manner as defined for the purposes of the present invention, the slope of the output curve at the inflection point is compared with the relative slope of a line between the first and last points of the transition region. For example, FIG. 4A shows a graph of an exemplary output function, f(x) along with aligned graphs of the first, f'(x), and second, f''(x), and third, f'''(x), derivatives of the exemplary output function. The output function f(x) describes the effect of the input (x or I) on the output or response (R(I)). For purposes of the present invention, the transition region is defined as the region between the relative maxima, $R(I_1)$, and the minima, $R(I_2)$, of the second derivative, f''(x), of the output function, f(x). The relative maxima, $R(I_1)$, and the relative minima, $R(I_2)$, are points at which the third derivative, f'''(x), equals zero. The inflection point, $I_0$, is defined as the point in the transition region at which the second derivative, f''(x), equals zero, i.e., $$\left. \frac{d^2 R}{dI^2} \right|_{I=I_0} = 0.$$

The comparison of the slope of the output function at the inflection point to the slope of a line between the first and the last points of the transition region can be described by the equation:

$$\left. \frac{dR}{dI} \right|_{I=I_0} = k \frac{(\Delta R_T)}{(\Delta I_T)}.$$

In this equation dR/dI at the inflection point is the first derivative of the output function at that point. The term $\Delta I_T$ is the change in the input to the responsive system between the first, $I_1$, and last, $I_2$, points of the transition region, i.e., $I_2 - I_1$, and the term $\Delta R_T$ is the change in the response of the output function between the first and last points of the transition region, i.e., $R(I_2) - R(I_1)$. The coefficient k is a proportional constant that describes the relative steepness of the slope of the output function at the inflection point, $I_0$, compared to the slope of a line between the first and last points of the transition region. In order that the responsive system have a discontinuous output function, the proportional constant k must be at least about 2.0, preferably at least about 3.0, more preferably at least about 5.0, even more preferably at least about 10.0, with at least about 100.0 being the most preferred.

Figure 4B:
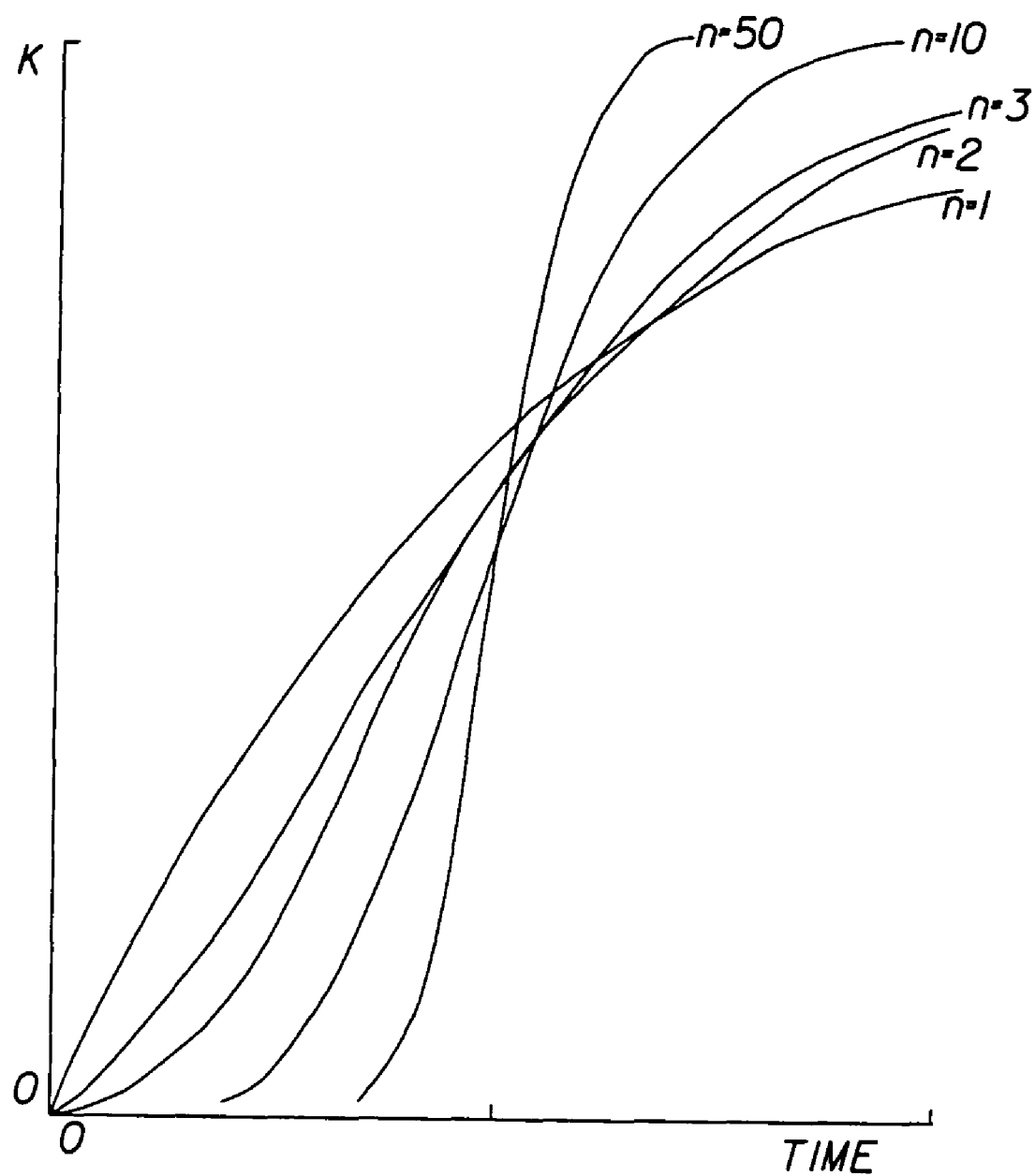
FIG. 4B shows a transfer function of a control system having a series of first order lags having an equal time constant.

In certain embodiments, the relative degree of steepness in the transition region of a discontinuous responsive system may also be modeled by a transfer function of a control system having a series of an integer number, n, first order lags with an equal time constant. The transfer function of the responsive system is defined for the purposes of the present invention as the ratio of the Laplace transforms of the output (responding variable) to the input (disturbing variable). See, e.g., Robert H. Perry & Don Green, *Perry's Chemical Engineers' Handbook*, Sixth Ed., Chap. 22 (McGraw Hill, Inc. 1984). As shown in FIG. 4B, the relative degree of steepness of an output function may be approximated by the formula: $KG(s) = K/Ts+1)^n$ in which KG(s) is the transfer function, K is a proportional element, T is the time constant of the system, and n is the integer number of first order time lags. In this model, as the number n increases, the steepness of the output function in the transition region increases, and the model begins to approximate a discontinuous responsive system. Certain discontinuous responsive systems of the present invention preferably may be modeled by the above formula when n is greater than or equal to about 25, with n being greater than or equal to about 50 being more preferred, and n being greater than or equal to about 100 being the most preferred.

As shown in FIG. 3A, a responsive system of the present invention may include a single threshold level at which the responsive system may release all of its stored energy to perform a specific responsive function or may include multiple threshold levels at which the system may release a pre-designated portion of its stored energy to perform one or more specific responsive functions at each of the threshold levels. In an embodiment having a single threshold level, for example, the responsive system may release all of its stored energy to perform the entire responsive function when that threshold level is met. In such a single threshold embodiment, In this example, the discontinuous responsive system includes a system that has two states such as on or off. When a threshold quantity of an input such as a target biological material is present in the absorbent article, the responsive system may perform a single responsive function upon the waste, the wearer, the article or a component thereof, such as enveloping the waste away from the skin of the user or providing an easily detectable visual signal to the wearer or caregiver. Thus, the discontinuous responsive system may perform a one-time "switch-like" function that changes from one state to another in the presence of a threshold level of an input.

Figure 3B:
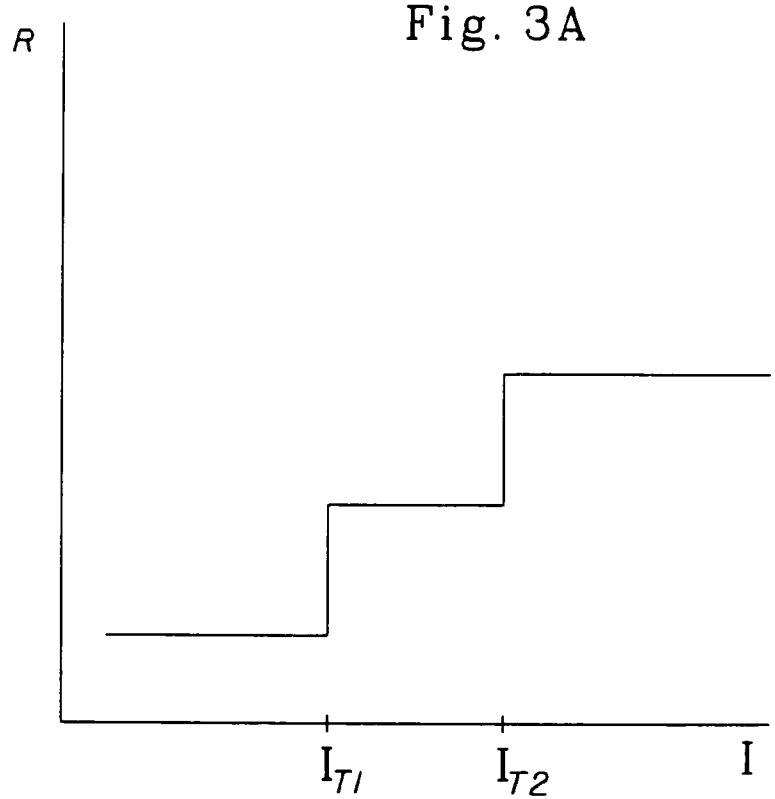
FIG. 3B shows an ideal output function of a discontinuous responsive system of the present invention having multiple threshold levels.

Alternatively, as shown in FIG. 3B, the responsive system may have multiple threshold levels at which when each threshold level is met the system may release a given "quanta" of energy or deliver a given quantity of material to perform a specific responsive function. In this embodiment, when each threshold level is met, a portion of the entire responsive function may be performed and/or different independent responsive functions may be performed in response to different threshold levels being met. For example, a responsive system may monitor a fecal enzyme and when each threshold enzyme level is met may deliver an equal or unequal quantity of enzyme inhibitor(s) or lotion, or deliver a pH buffer at the first threshold level and perform another responsive function such as delivering a quantity of enzyme inhibitor(s) at the second threshold level. In each transition region, the responsive system responds essentially the same as the transition region in the single threshold embodiment described above.

In addition, a responsive system may monitor multiple inputs such as one or more pathogenic bacteria and/or one or more fecal enzymes and perform one or more responsive functions when the threshold levels of the different inputs are met or may perform one responsive function only when two or more of the threshold levels of the different inputs are met. Thus, a controller may monitor multiple different inputs and perform a different responsive function when the threshold level of the different inputs are met. Alternatively, the controller may perform a logic OR-gate type function such that a responsive function may be performed when one or more threshold levels of the multiple inputs are met. The controller may also perform a logic AND-gate type function such that a responsive function may be performed when each threshold level of two or more different inputs is met.

The responsive system may also comprise a "closed loop" or an "open loop" system. A "closed loop" system, which is also referred to as a "feedback control loop" system, includes distinct biosensor 60 and actuator components and performs a responsive function upon the input. In some preferred embodiments, the system may also use a detection or a measurement of an element or a parameter of the output condition as at least one trigger of the responsive function that is performed upon the input. The output condition may be the state of the input condition after the actuator has had the opportunity to perform a responsive function on the input condition. The responsive function may be performed when the output condition reaches a threshold level, or may be performed only when the output condition and one or more other conditions are met. Acting upon the input may include acting upon the element sensed, e.g., sensing a microorganism and acting upon the microorganism, or may include acting upon a composition of which the element sensed is an integral component, e.g., sensing a fecal bacteria and acting upon the fecal mass or residual feces on the wearer's skin As described above, a feedback control loop system includes at least two distinct components: the biosensor 60 and the actuator. The biosensor 60 detects an event, or a parameter associated with that event. The actuator receives a signal and performs a responsive function on the input condition detected by the biosensor 60. The feedback control loop may further include a controller. In this case, the biosensor 60 may provide a signal to the controller, and the controller may direct the actuator to perform a responsive function upon the input condition. The controller may be a separate component of the responsive system or the controller function may be performed by the biosensor 60 and/or the actuator.

The feedback control loop may be "non-modulating" or "modulating." In a "non-modulating" feedback control loop responsive system the responsive system acts as a one-time switch in which the actuator performs a responsive function on the input when the threshold level of the output condition is met. For example, the biosensor 60 may detect the presence of or measure the concentration of a specific pathogenic microorganism, and the actuator may signal the caretaker of a potential incipient infection. In this example, the actuator acts upon the input detected by the biosensor 60. A "modulating" feedback control loop, however, includes a biosensor 60, an actuator and a controller. In a modulating feedback control loop, the output condition is monitored constantly or repeatedly, and the controller directs the actuator to perform a responsive function on the input in order to maintain the output condition at a desired set point or within a desired range or to provide a continuous measurement of the level or concentration of the target biological analyte.

An "open loop" system, however, is a system that responds to the input to perform a responsive function without using feedback, i.e., the output has no effect upon the sensed input entering the system. An open loop system may include a responsive system that has a single device that performs the functions of both the biosensor 60 and the actuator or may have distinct biosensor 60 and actuator components in which the actuator acts upon something other than the input. A super absorbent polymer placed in an absorbent core of a disposable absorbent article, for example, provides an open loop response because the polymer only includes a single device that performs the functions of the biosensor 60 and actuator. Alternatively, an open loop responsive system may include a biosensor 60 that detects bodily waste or a component of that bodily waste, and an actuator that performs a responsive function in a continuous or a discontinuous manner on something other than the input detected by the biosensor 60.

The present invention includes responsive systems that provide a discontinuous or continuous response, whether open loop or closed loop. Other responsive systems are described in U.S. patent application Ser. Nos. 09/106,424 entitled "Disposable Article Having A Discontinuous Responsive System" filed on Jun. 29, 1998 (P&G Case Number 7197); Ser. No. 09/107,563 entitled "Disposable Article Having A Responsive System Including A Feedback Control Loop" filed on Jun. 29, 1998 (P&G Case Number 7198); and Ser. No. 09/106,225 entitled "Disposable Article Having A Responsive System Including A Mechanical Actuator" filed on Jun. 29, 1998 (P&G Case Number 7199), each of which is incorporated herein by reference.

An example of a diaper 20 of the present invention may include a responsive system that includes a biosensor 60 as shown in FIG. 1 and an actuator as shown in FIG. 2. In this embodiment, the biosensor 60 may comprise a transducer operatively associated with a bio-recognition element adapted to detect E. coli in feces. Upon the specific detection of a threshold level of E. coli by the bio-recognition element, the transducer signals the actuator with an electrical current. The article shown in FIG. 1 may include an actuator that comprises a compressed resilient material 94 vacuum sealed under a water soluble film 91, as shown in FIG. 2 (e.g., a PVA film). Upon receipt of the proper signal from the biosensor 60, the actuator may close a switch, for example may release a small amount of stored water to contact and dissolve the water soluble film 91. This results in the release of the stored mechanical energy in the compressed foam. The resilient material 94 expands and forms a spacer to provide void volume for the incipient feces. Alternatively, the switch closure may additionally release an antimicrobial to control the E. coli and/or a visible dye to signal the E. coli presence to the wearer or caretaker. In another embodiment, the responsive system may include an actuator that alerts the caretaker or the wearer of an impending event such as a diarrheal infection or a skin irritation (e.g., candidiasis).

Test Method

Response Factor Test:

With the Response Factor Test as described hereafter, the response of a quantitative sensor as a reaction to exposure to a specific substance or composition can be measured.

The specific substances or compositions for which this test is suitable include: fecal test material in aqueous solution having a concentration of 1 gram of fecal test material per 1 gram of physiological saline solution; fecal test material in test urine solution having a concentration of 1 gram of fecal material per 1 gram of test urine solution; test urine solution; a solution of skatole in physiological saline solution having a concentration of 180 micrograms of skatole per gram of physiological saline solution; physiological saline solution.

All measurements are carried at body temperature (37° Celsius). The method includes the following steps in the following order:
1) Record quantitative response of the sensor after exposure to physiological saline solution for 24 hours. The background response is the maximum recorded response.
2) Expose the sensor to specified substance or composition.
3) Record quantitative response of the sensor while sensor is still exposed to the specified substance or composition for 24 hours. Substance response is the maximum recorded response.

The Response Factor is obtained by normalizing the substance response with the background response. In case the Response Factor is smaller than 1, the reciprocal value of the Response Factor is reported as the Response Factor (i.e., the response may be inversely correlated with the input).

While particular embodiments and/or individual features of the present invention have been illustrated and described, it would be obvious to those skilled in the art that various other changes and modifications can be made without departing from the spirit and scope of the invention. For example, although the present invention is illustrated and described primarily with respect to a disposable diaper, the present invention is not limited to this embodiment. The present invention may also be used, for example, in articles that are applied directly to a wearer (e.g., to the perianal or perineal regions of the wearer) prior to the application of a disposable diaper or in place of a disposable diaper, in a pull-on diaper, a diaper insert, a sanitary napkin, a tampon, etc. Further, it should be apparent that all combinations of such embodiments and features are possible and can result in preferred executions of the invention. Therefore, the appended claims are intended to cover all such changes and modifications that are within the scope of this invention.

What is claimed is:

1. A disposable article to be fitted to a wearer comprising: a biosensor including at least one biologically reactive bio-recognition element comprising a biologically derived material and adapted to detect or interact selectively with a specific microorganism selected from the group consisting of pathogenic bacteria, colonic bacteria, viruses, parasites and fungi, present in bodily waste or on the wearer's skin, the biosensor also being adapted to provide a signal of detection of the specific microorganism.

2. The disposable article of claim 1 wherein the biosensor is selected from the group of: a biocatalytic biosensor and a bioaffinity biosensor.

3. The disposable article of claim 2 wherein the bioaffinity biosensor is selected from the group of: a chemoreceptor-based biosensor and an immunosensor.

4. The disposable article of claim 1 wherein the bio-recognition element is selected from the list including: an enzyme or sequence of enzymes; an antibody; DNA; an organelle; a membrane receptor protein; a natural or synthetic cell membrane; viable or nonviable bacterial, plant, or animal cells; at least a portion of a nerve bundle; at least a portion of a sensing organ.

5. The disposable absorbent article of claim 4 wherein the bio-recognition element is selected from the group including *Acinetobacter baumannii* TO136 and *Bacillus* sp TO141.

6. The disposable absorbent article of claim 5 wherein the bio-recognition element is disposed on a substrate selected from the group of: polymer based materials, hydrogels, tissues, nonwoven materials, and woven materials.

7. The disposable article of claim 1 wherein the specific microorganism is selected from the group consisting of rotavirus, rhinovirus, human immunodeficiency virus, a parasite, and a pathogenic bacteria selected from the list: *Escherichia coli; Salmonella typhi; Salmonella paratyphi; Salmonella enteriditis; Salmonella typhimurium; Salmonella heidelberg; Shigella sonnei; Shigella flexneri; Shigella boydii; Shigella dysenteriae; Vibrio cholerae; Mycobacterium tuberculosis; Yersinia enterocolitica; Aeromonas hydrophila; Plesiomonas shigelloides; Campylobacter jejuni; Campylobacter coli; Bacteroides fragilis; Clostridia septicum, Clostridia perfringens, Clostridia botulinum*, and *Clostridia difficile*.

8. The disposable article of claim 1 wherein the biosensor detects a target biological analyte associated with a systemic or skin health condition in the wearer prior to the onset of clinically observable symptoms of the condition.

9. The disposable article of claim 1 wherein the biosensor detects a target biological analyte only above a pre-defined threshold level.

10. The disposable article of claim 1 wherein the biosensor provides a signal to at least one of the group of: the wearer, a caretaker, an actuator.

11. The disposable article of claim 10 wherein the signal is a visible indication.

12. The disposable article of claim 10 wherein the signal is qualitative.

13. The disposable article of claim 10 wherein the signal is quantitative.

14. The disposable article of claim 10 wherein the signal is durable throughout at least the usage life of the article.

15. The disposable article of claim 1 wherein the article additionally comprises a cleaning element for the biosensor.

16. The disposable article of claim 1 wherein the biosensor is affixed to a support element.

17. The disposable article of claim 1 wherein the support element adheres to the wearer's skin.

18. The disposable article of claim 16 wherein the support element is an adhesive tape.

19. The disposable article of claim 1 wherein the biosensor is detachable from the article.

20. The disposable article of claim 1 wherein the biosensor adheres to the wearer's skin.

21. The disposable article of claim 1 wherein the bodily waste is feces, urine or menses.

22. The disposable article of claim 1 wherein the bodily waste is residual fecal contamination located on the wearer's skin.

23. The disposable article of claim 1 further comprising an actuator that performs a responsive function when the biosensor detects a target biological analyte.

24. The disposable article of claim 23 wherein the responsive function is a signal to a caretaker, or the wearer.

25. The disposable article of claim 23 wherein the actuator transforms a potential energy to perform the responsive function, the potential energy being one or more selected from the group of: mechanical energy, electrical energy and chemical energy.

26. The disposable article of claim 23 wherein the responsive function is one or more selected from the group of: creating a void volume, treating skin, creating a foaming system and signaling a caregiver.

27. The disposable article of claim 1 further comprising a receiver.

28. The disposable article of claim 27 wherein the receiver is integral with said article.

29. The disposable article of claim 27 further comprising a transmitter.

30. The disposable article of claim 29 wherein the transmitter comprises an infrared telemetry transmitter.

31. The disposable article of claim 1 wherein the biosensor has a Response Factor of at least 5 when exposed to feces.

32. The disposable article of claim 1 wherein the biosensor has a Response Factor of at least 10 when exposed to feces.

33. The disposable article of claim 1 wherein the biosensor has a Response Factor of at least 20 when exposed to feces.

34. The disposable absorbent article of claim 1 wherein the biosensor has a Response Factor of at least 5 when exposed to a solution of skatole in physiological saline solution having a concentration of 180 micrograms of skatole per gram of physiological saline solution.

35. The disposable absorbent article of claim 1 wherein the specific microorganism is selected from the group consisting of rotavirus, rhinovirus, human immunodeficiency virus, a parasite, and a pathogenic bacteria selected from the list: *Escherichia coli; Salmonella typhi; Salmonella paratyphi; Salmonella enteriditis; Salmonella typhimurium; Salmonella heidelberg; Shigella sonnei; Shigella flexneri; Shigella boydii; Shigella dysenteriae; Vibrio cholerae; Mycobacterium tuberculosis; Yersinia enterocolitica; Aeromonas hydrophila; Plesiomonas shigelloides; Campylobacter jejuni; Campylobacter coli; Bacteroides fragilis; Clostridia septicum, Clostridia perfringens, Clostridia botulinum*, and *Clostridia difficile*.

36. A disposable absorbent article to be fitted to a wearer comprising:
a topsheet;
a backsheet joined with the topsheet;
an absorbent core disposed between the topsheet and the backsheet; and
a biosensor disposed on the disposable article, the biosensor including at least one biologically reactive bio-recognition element comprising a biologically derived material and adapted to detect or interact selectively with a specific microorganism selected from the group consisting of pathogenic bacteria, colonic bacteria, viruses, parasites and fungi, present in bodily waste, the biosensor also being adapted to provide a signal of detection of the specific microorganism.

37. The disposable absorbent article of claim 36 wherein the disposable article is chosen from the following group: a sanitary napkin, a diaper, a training pant and an adult incontinence device.

38. The disposable absorbent article of claim 36 wherein the biosensor is selected from the group of: a biocatalytic biosensor and a bioaffinity biosensor.

39. The disposable absorbent article of claim 38 wherein the bioaffinity biosensor is selected from the group of: a chemoreceptor-based biosensor and an immunosensor.

40. The disposable absorbent article of claim 36 wherein the bio-recognition element is selected from the list including: an enzyme or sequence of enzymes; an antibody; DNA; an organelle; a membrane receptor protein; a natural or synthetic cell membrane; viable or nonviable bacterial, plant, or animal cells; at least a portion of a nerve bundle; at least a portion of a sensing organ.

41. The disposable absorbent article of claim 36 wherein the biosensor adheres to the wearer's skin.

42. The disposable absorbent article of claim 36 wherein the biosensor has a Response Factor of at least 5 when exposed to feces.

43. The disposable absorbent article of claim 36 wherein the biosensor has a Response Factor of at least 10 when exposed to feces.

44. The disposable absorbent article of claim 36 wherein the biosensor has a Response Factor of at least 20 when exposed to feces.

45. The disposable absorbent article of claim 36 wherein the biosensor has a Response Factor of at least 5 when exposed to a solution of skatole in physiological saline solution having a concentration of 180 micrograms of skatole per gram of physiological saline solution.

* * * * *

UNITED STATES PATENT AND TRADEMARK OFFICE
CERTIFICATE OF CORRECTION

PATENT NO. : 7,982,088 B2
APPLICATION NO. : 10/753669
DATED : July 19, 2011
INVENTOR(S) : Roe et al.

It is certified that error appears in the above-identified patent and that said Letters Patent is hereby corrected as shown below:

Column 5

Line 19, delete "Imobilizing" and insert --Immobilizing--.

Column 15

Line 38, after the word biosensor, delete "to".

Column 18

Line 18, delete "SIF/210PPI" and insert --SIF/2I0PP1--.

Signed and Sealed this
Tenth Day of April, 2012

David J. Kappos
*Director of the United States Patent and Trademark Office*